(12) United States Patent
Selby et al.

(10) Patent No.: US 12,161,792 B2
(45) Date of Patent: Dec. 10, 2024

(54) FLUID COLLECTION APPARATUS

(71) Applicant: CONVATEC LIMITED, Flintshire (GB)

(72) Inventors: Robert Gordon Maurice Selby, Flintshire (GB); Simon John Weddelow, Flintshire (GB); Lawrence Mark Baker, Flintshire (GB)

(73) Assignee: CONVATEC LIMITED, Flintshire (GB)

( * ) Notice: Subject to any disclaimer, the term of this patent is extended or adjusted under 35 U.S.C. 154(b) by 288 days.

(21) Appl. No.: 16/764,272

(22) PCT Filed: Nov. 16, 2018

(86) PCT No.: PCT/IB2018/001417
§ 371 (c)(1),
(2) Date: May 14, 2020

(87) PCT Pub. No.: WO2019/097288
PCT Pub. Date: May 23, 2019

(65) Prior Publication Data
US 2020/0345903 A1    Nov. 5, 2020

(30) Foreign Application Priority Data

Nov. 16, 2017 (GB) ....................................... 1719014
Nov. 16, 2017 (GB) ....................................... 1719027

(51) Int. Cl.
*A61M 1/00* (2006.01)

(52) U.S. Cl.
CPC .............. *A61M 1/784* (2021.05); *A61M 1/60* (2021.05); *A61M 1/88* (2021.05); *A61M 1/98* (2021.05); *A61M 2205/7536* (2013.01)

(58) Field of Classification Search
CPC ...... A61M 1/0001; A61M 1/60; A61M 1/784; A61M 1/88; A61M 1/90; A61M 1/98; A61M 2205/7536; A61M 2205/21; A61M 2209/088
See application file for complete search history.

(56) References Cited

U.S. PATENT DOCUMENTS

| | | |
|---|---|---|
| 10,016,537 B2 | 7/2018 | Menon et al. |
| 10,046,096 B2 | 8/2018 | Askem et al. |
| 10,076,447 B2 | 9/2018 | Barta et al. |
| 10,076,587 B2 | 9/2018 | Locke et al. |
| 10,143,784 B2 | 12/2018 | Walton et al. |
| 10,426,670 B2 | 10/2019 | von Blucher et al. |
| 10,426,747 B2 | 10/2019 | Johnson |
| 10,426,874 B2 | 10/2019 | Chien et al. |
| 10,426,875 B2 | 10/2019 | Blott et al. |
| 10,426,938 B2 | 10/2019 | Locke et al. |
| 10,434,015 B2 | 10/2019 | Taylor et al. |

(Continued)

FOREIGN PATENT DOCUMENTS

| | | |
|---|---|---|
| EP | 3187204 A1 | 7/2017 |
| EP | 3556407 A1 | 10/2019 |

(Continued)

*Primary Examiner* — Jessica Arble
*Assistant Examiner* — Alessandro R Del Priore
(74) *Attorney, Agent, or Firm* — Taft Stettinius & Hollister LLP; Ryan O. White; Derek B. Lavender

(57) ABSTRACT

Fluid collection apparatuses and methods of use in negative pressure therapies are provided.

16 Claims, 18 Drawing Sheets

(56) References Cited

U.S. PATENT DOCUMENTS

| | | |
|---|---|---|
| 10,434,142 B2 | 10/2019 | Niazi et al. |
| 10,434,210 B2 | 10/2019 | Olson et al. |
| 10,434,284 B2 | 10/2019 | Hanson et al. |
| 10,449,094 B2 | 10/2019 | Donda et al. |
| D866,756 S | 11/2019 | Allen et al. |
| 10,463,760 B2 | 11/2019 | Karthikeyan et al. |
| 10,463,773 B2 | 11/2019 | Haggstrom et al. |
| 10,470,933 B2 | 11/2019 | Riesinger |
| 10,470,936 B2 | 11/2019 | Wohlgemuth et al. |
| 10,471,122 B2 | 11/2019 | Shi et al. |
| 10,471,190 B2 | 11/2019 | Locke et al. |
| 10,478,345 B2 | 11/2019 | Barta et al. |
| 10,478,346 B2 | 11/2019 | Knutson |
| 10,478,394 B2 | 11/2019 | Yu |
| 10,485,707 B2 | 11/2019 | Sexton |
| 10,485,891 B2 | 11/2019 | Andrews et al. |
| 10,485,892 B2 | 11/2019 | Hands et al. |
| 10,485,906 B2 | 11/2019 | Freedman et al. |
| 10,486,135 B2 | 11/2019 | Yang et al. |
| 10,492,956 B2 | 12/2019 | Zamierowski |
| 10,493,178 B2 | 12/2019 | Marchant et al. |
| 10,493,184 B2 | 12/2019 | Collinson et al. |
| 10,493,185 B2 | 12/2019 | Stokes et al. |
| 10,500,099 B2 | 12/2019 | Hung et al. |
| 10,500,103 B2 | 12/2019 | Croizat et al. |
| 10,500,104 B2 | 12/2019 | Sookraj |
| 10,500,173 B2 | 12/2019 | Yang et al. |
| 10,500,235 B2 | 12/2019 | Wardell |
| 10,500,300 B2 | 12/2019 | Dybe et al. |
| 10,500,301 B2 | 12/2019 | Laurensou |
| 10,500,302 B2 | 12/2019 | Holm et al. |
| 10,501,487 B2 | 12/2019 | Andrews et al. |
| 10,506,928 B2 | 12/2019 | Locke et al. |
| 10,507,141 B2 | 12/2019 | Allen et al. |
| 10,507,259 B2 | 12/2019 | Cree et al. |
| 10,512,707 B2 | 12/2019 | Whalen, III et al. |
| 10,525,170 B2 | 1/2020 | Havenstrite et al. |
| 10,532,137 B2 | 1/2020 | Pratt et al. |
| 10,532,194 B2 | 1/2020 | Locke et al. |
| 10,537,657 B2 | 1/2020 | Phillips et al. |
| 10,542,936 B2 | 1/2020 | Goldberg et al. |
| 10,543,133 B2 | 1/2020 | Shaw et al. |
| 10,543,293 B2 | 1/2020 | Suschek |
| 10,548,777 B2 | 2/2020 | Locke et al. |
| 10,549,008 B2 | 2/2020 | Yoo |
| 10,549,016 B2 | 2/2020 | Bushko et al. |
| 10,549,017 B2 | 2/2020 | Hsiao et al. |
| 10,555,838 B2 | 2/2020 | Wu et al. |
| 10,555,839 B2 | 2/2020 | Hartwell |
| 10,556,044 B2 | 2/2020 | Robinson et al. |
| 10,561,533 B2 | 2/2020 | Hoggarth et al. |
| 10,561,536 B2 | 2/2020 | Holm et al. |
| 10,568,767 B2 | 2/2020 | Addison et al. |
| 10,568,768 B2 | 2/2020 | Long et al. |
| 10,568,770 B2 | 2/2020 | Robinson et al. |
| 10,568,771 B2 | 2/2020 | MacDonald et al. |
| 10,568,773 B2 | 2/2020 | Tuck et al. |
| 10,568,983 B2 | 2/2020 | Gerdes et al. |
| 10,575,991 B2 | 3/2020 | Dunn |
| 10,575,992 B2 | 3/2020 | Sarangapani et al. |
| 10,576,037 B2 | 3/2020 | Harrell |
| 10,576,189 B2 | 3/2020 | Locke et al. |
| 10,583,042 B2 | 3/2020 | Sarangapani et al. |
| 10,583,228 B2 | 3/2020 | Shuler et al. |
| 10,589,007 B2 | 3/2020 | Coulthard et al. |
| 10,590,184 B2 | 3/2020 | Kuo |
| 10,610,414 B2 | 4/2020 | Hartwell et al. |
| 10,610,415 B2 | 4/2020 | Griffey et al. |
| 10,610,623 B2 | 4/2020 | Robinson et al. |
| 10,617,569 B2 | 4/2020 | Bonn |
| 10,617,608 B2 | 4/2020 | Shin et al. |
| 10,617,769 B2 | 4/2020 | Huang |
| 10,617,784 B2 | 4/2020 | Yu et al. |
| 10,617,786 B2 | 4/2020 | Kluge et al. |
| 10,618,266 B2 | 4/2020 | Wright et al. |
| 10,624,984 B2 | 4/2020 | Courage et al. |
| 10,625,002 B2 | 4/2020 | Locke et al. |
| 10,632,019 B2 | 4/2020 | Vitaris |
| 10,632,224 B2 | 4/2020 | Hardy et al. |
| 10,639,206 B2 | 5/2020 | Hu et al. |
| 10,639,350 B2 | 5/2020 | Arber et al. |
| 10,639,404 B2 | 5/2020 | Lichtenstein |
| 10,646,614 B2 | 5/2020 | Grinstaff et al. |
| 10,653,562 B2 | 5/2020 | Robinson et al. |
| 10,653,782 B2 | 5/2020 | Ameer et al. |
| 10,653,810 B2 | 5/2020 | Datt et al. |
| 10,653,821 B2 | 5/2020 | Nichols |
| 10,653,823 B2 | 5/2020 | Bharti et al. |
| 10,660,799 B2 | 5/2020 | Wu et al. |
| 10,660,851 B2 | 5/2020 | Millis et al. |
| 10,660,992 B2 | 5/2020 | Canner et al. |
| 10,660,994 B2 | 5/2020 | Askem et al. |
| 10,667,955 B2 | 6/2020 | Allen et al. |
| 10,667,956 B2 | 6/2020 | Van Holten et al. |
| 10,682,257 B2 | 6/2020 | Lu |
| 10,682,258 B2 | 6/2020 | Manwaring et al. |
| 10,682,259 B2 | 6/2020 | Hunt et al. |
| 10,682,318 B2 | 6/2020 | Twomey et al. |
| 10,682,386 B2 | 6/2020 | Ellis-Behnke et al. |
| 10,682,446 B2 | 6/2020 | Askem et al. |
| 10,687,983 B2 | 6/2020 | Dahlberg et al. |
| 10,687,985 B2 | 6/2020 | Lee et al. |
| 10,688,215 B2 | 6/2020 | Munro et al. |
| 10,688,217 B2 | 6/2020 | Hanson et al. |
| RE48,117 E | 7/2020 | Albert et al. |
| 10,702,419 B2 | 7/2020 | Locke et al. |
| 10,702,420 B2 | 7/2020 | Hammond et al. |
| 10,703,942 B2 | 7/2020 | Tunius |
| 10,709,760 B2 | 7/2020 | Gronberg et al. |
| 10,709,807 B2 | 7/2020 | Kshirsagar |
| 10,709,883 B2 | 7/2020 | Spector |
| 10,716,711 B2 | 7/2020 | Locke et al. |
| 10,716,874 B2 | 7/2020 | Koyama et al. |
| 10,729,589 B2 | 8/2020 | Dorian et al. |
| 10,729,590 B2 | 8/2020 | Simmons et al. |
| 10,729,826 B2 | 8/2020 | Lin |
| 10,736,787 B2 | 8/2020 | Hannigan et al. |
| 10,736,788 B2 | 8/2020 | Locke et al. |
| 10,736,985 B2 | 8/2020 | Odermatt et al. |
| 10,737,003 B2 | 8/2020 | Fujisaki |
| 10,743,900 B2 | 8/2020 | Ingram et al. |
| 10,744,040 B2 | 8/2020 | Kazala, Jr. et al. |
| 10,744,041 B2 | 8/2020 | Hartwell |
| 10,744,225 B2 | 8/2020 | Lindgren et al. |
| 10,744,237 B2 | 8/2020 | Guidi et al. |
| 10,744,238 B2 | 8/2020 | Guidi et al. |
| 10,744,239 B2 | 8/2020 | Armstrong et al. |
| 10,744,240 B2 | 8/2020 | Simmons et al. |
| 10,751,212 B2 | 8/2020 | Raza et al. |
| 10,751,442 B2 | 8/2020 | Bonnefin et al. |
| 10,751,452 B2 | 8/2020 | Topaz |
| 10,758,423 B2 | 9/2020 | Pigg et al. |
| 10,758,424 B2 | 9/2020 | Blott et al. |
| 10,758,425 B2 | 9/2020 | Blott et al. |
| 10,758,426 B2 | 9/2020 | Eddy |
| 10,758,651 B2 | 9/2020 | Blott et al. |
| 10,765,561 B2 | 9/2020 | Lattimore et al. |
| 10,765,783 B2 | 9/2020 | Locke et al. |
| 10,772,767 B2 | 9/2020 | Bjork et al. |
| 10,772,999 B2 | 9/2020 | Svensby |
| 10,779,993 B2 | 9/2020 | Bishop et al. |
| 10,780,114 B2 | 9/2020 | Udagawa et al. |
| 10,780,194 B2 | 9/2020 | Flach et al. |
| 10,780,201 B2 | 9/2020 | Lin |
| 10,780,202 B2 | 9/2020 | Askem et al. |
| 10,780,203 B2 | 9/2020 | Coulthard et al. |
| 10,782,238 B2 | 9/2020 | Hicks et al. |
| 10,792,191 B2 | 10/2020 | Robinson et al. |
| 10,792,192 B2 | 10/2020 | Tout et al. |
| 10,792,337 B2 | 10/2020 | Leung et al. |
| 10,792,404 B2 | 10/2020 | Hu et al. |
| 10,792,482 B2 | 10/2020 | Randolph et al. |
| 10,800,905 B2 | 10/2020 | Delli-Santi et al. |
| 10,806,819 B2 | 10/2020 | Shuler |

(56) References Cited

U.S. PATENT DOCUMENTS

| | | |
|---|---|---|
| 11,026,847 B2 | 6/2021 | Piotrowski et al. |
| 11,058,587 B2 | 7/2021 | Adie et al. |
| 11,058,588 B2 | 7/2021 | Albert et al. |
| 11,071,652 B2 | 7/2021 | Donda et al. |
| 11,071,653 B2 | 7/2021 | Hunt |
| 11,076,997 B2 | 8/2021 | Hunt et al. |
| 11,083,884 B2 | 8/2021 | Robinson et al. |
| 11,090,195 B2 | 8/2021 | Adie et al. |
| 11,096,829 B2 | 8/2021 | Robinson et al. |
| 11,123,476 B2 | 9/2021 | Hunt et al. |
| 11,123,537 B2 | 9/2021 | Luckemeyer et al. |
| 11,135,342 B2 | 10/2021 | Pratt et al. |
| 11,141,521 B2 | 10/2021 | Beadle et al. |
| 11,154,426 B2 | 10/2021 | Riesinger |
| 11,154,649 B2 | 10/2021 | Collinson et al. |
| 11,179,276 B2 | 11/2021 | Hartwell |
| 11,179,512 B2 | 11/2021 | Locke et al. |
| 11,191,887 B2 | 12/2021 | Locke et al. |
| 11,197,953 B2 | 12/2021 | Heaton et al. |
| 11,207,442 B2 | 12/2021 | Locke et al. |
| 11,207,458 B2 | 12/2021 | Locke et al. |
| 11,246,758 B2 | 2/2022 | Hardman et al. |
| 11,246,975 B2 | 2/2022 | Locke et al. |
| 11,253,400 B2 | 2/2022 | Zochowski et al. |
| 11,253,401 B2 | 2/2022 | Pratt et al. |
| 11,266,537 B2 | 3/2022 | Robinson et al. |
| 11,266,774 B2 | 3/2022 | Selby et al. |
| 11,278,454 B2 | 3/2022 | Edwards et al. |
| 11,298,268 B2 | 4/2022 | Jardret et al. |
| 11,298,454 B2 | 4/2022 | Weston |
| 11,318,243 B2 | 5/2022 | Robinson et al. |
| 11,351,063 B2 | 6/2022 | Locke et al. |
| 11,351,064 B2 | 6/2022 | Hartwell |
| 11,364,151 B2 | 6/2022 | Hartwell |
| 11,364,334 B2 | 6/2022 | Long et al. |
| 11,864,980 B2 | 1/2024 | Locke et al. |
| 11,864,981 B2 | 1/2024 | Allen et al. |
| 11,878,102 B2 | 1/2024 | Cornet et al. |
| 11,883,261 B2 | 1/2024 | Coulthard et al. |
| 11,883,262 B2 | 1/2024 | Cole et al. |
| 11,883,577 B2 | 1/2024 | Selby et al. |
| 11,883,578 B2 | 1/2024 | Locke et al. |
| 11,890,437 B2 | 2/2024 | Luckemeyer et al. |
| 11,896,465 B2 | 2/2024 | Askem et al. |
| 11,903,798 B2 | 2/2024 | Askem et al. |
| 11,911,556 B2 | 2/2024 | Mercer et al. |
| 11,925,735 B2 | 3/2024 | Gowans et al. |
| 11,931,165 B2 | 3/2024 | Askem et al. |
| 11,938,002 B2 | 3/2024 | Hunt et al. |
| 11,944,519 B2 | 4/2024 | Zurovcik |
| 11,944,520 B2 | 4/2024 | Locke et al. |
| 11,957,545 B2 | 4/2024 | Hunt et al. |
| 11,957,829 B2 | 4/2024 | Coulthard et al. |
| 11,963,850 B2 | 4/2024 | Freedman et al. |
| 11,964,093 B2 | 4/2024 | Greener |
| 11,969,541 B2 | 4/2024 | Gordon et al. |
| 11,974,902 B2 | 5/2024 | Greener |
| 11,975,134 B2 | 5/2024 | Quintanar |
| 11,992,392 B2 | 5/2024 | Earl et al. |
| 11,992,601 B2 | 5/2024 | Vess et al. |
| 12,004,925 B2 | 6/2024 | Hartwell |
| 12,016,991 B2 | 6/2024 | Coulthard et al. |
| 2006/0155260 A1 | 7/2006 | Blott et al. |
| 2006/0172000 A1 | 8/2006 | Cullen et al. |
| 2007/0185426 A1 | 8/2007 | Ambrosio et al. |
| 2007/0219512 A1 | 9/2007 | Heaton et al. |
| 2007/0239078 A1 | 10/2007 | Jaeb |
| 2008/0071214 A1* | 3/2008 | Locke .................. A61N 5/0616 604/151 |
| 2009/0234307 A1 | 9/2009 | Vitaris |
| 2009/0259203 A1 | 10/2009 | Hu et al. |
| 2009/0292263 A1 | 11/2009 | Hudspeth et al. |
| 2009/0293887 A1 | 12/2009 | Wilkes et al. |
| 2009/0299303 A1 | 12/2009 | Seegert |
| 2009/0306630 A1 | 12/2009 | Locke et al. |
| 2010/0015208 A1 | 1/2010 | Kershaw et al. |
| 2010/0030178 A1 | 2/2010 | MacMeccan et al. |
| 2010/0125233 A1 | 5/2010 | Edward S. et al. |
| 2010/0125258 A1 | 5/2010 | Coulthard et al. |
| 2010/0137775 A1 | 6/2010 | Hu et al. |
| 2010/0179493 A1* | 7/2010 | Heagle .................. A61M 1/90 604/313 |
| 2010/0185163 A1 | 7/2010 | Heagle |
| 2010/0286638 A1 | 11/2010 | Malhi |
| 2010/0298790 A1 | 11/2010 | Guidi et al. |
| 2010/0318071 A1 | 12/2010 | Wudyka |
| 2011/0015595 A1 | 1/2011 | Robinson et al. |
| 2011/0028918 A1 | 2/2011 | Hartwell |
| 2011/0112457 A1 | 5/2011 | Holm et al. |
| 2011/0178451 A1 | 7/2011 | Robinson et al. |
| 2011/0224593 A1 | 9/2011 | Tunius |
| 2011/0224630 A1 | 9/2011 | Simmons et al. |
| 2011/0230849 A1 | 9/2011 | Coulthard et al. |
| 2011/0251566 A1 | 10/2011 | Zimnitsky et al. |
| 2011/0257572 A1 | 10/2011 | Locke et al. |
| 2011/0257573 A1 | 10/2011 | Hong et al. |
| 2011/0275972 A1 | 11/2011 | Rosenberg |
| 2012/0071845 A1 | 3/2012 | Hu et al. |
| 2012/0130332 A1 | 5/2012 | Cotton et al. |
| 2012/0136325 A1 | 5/2012 | Allen et al. |
| 2012/0209226 A1 | 8/2012 | Simmons et al. |
| 2013/0053795 A1 | 2/2013 | Coulthard et al. |
| 2013/0053797 A1* | 2/2013 | Locke .................. A61M 1/86 604/319 |
| 2013/0066301 A1* | 3/2013 | Locke .................. A61M 1/78 604/317 |
| 2013/0123728 A1 | 5/2013 | Pratt et al. |
| 2013/0226063 A1 | 8/2013 | Taylor et al. |
| 2014/0005618 A1 | 1/2014 | Locke et al. |
| 2014/0074053 A1* | 3/2014 | Locke .................. A61M 1/90 156/60 |
| 2014/0188060 A1 | 7/2014 | Robinson et al. |
| 2014/0194838 A1 | 7/2014 | Wibaux et al. |
| 2014/0200532 A1 | 7/2014 | Robinson et al. |
| 2014/0236112 A1 | 8/2014 | Von Wolff et al. |
| 2014/0256925 A1 | 9/2014 | Catchmark et al. |
| 2014/0276497 A1* | 9/2014 | Robinson .............. A61M 1/884 604/319 |
| 2014/0276499 A1 | 9/2014 | Locke et al. |
| 2014/0296804 A1 | 10/2014 | Hicks et al. |
| 2014/0308338 A1 | 10/2014 | Nierle et al. |
| 2014/0309574 A1 | 10/2014 | Cotton |
| 2015/0018433 A1 | 1/2015 | Leipzig et al. |
| 2015/0057624 A1 | 2/2015 | Simmons et al. |
| 2015/0071985 A1 | 3/2015 | Walker et al. |
| 2015/0079152 A1 | 3/2015 | Wuollett et al. |
| 2015/0094674 A1 | 4/2015 | Pratt et al. |
| 2015/0104486 A1 | 4/2015 | Bonnefin et al. |
| 2015/0112311 A1 | 4/2015 | Hammond et al. |
| 2015/0119831 A1 | 4/2015 | Robinson et al. |
| 2015/0119834 A1 | 4/2015 | Locke et al. |
| 2015/0141941 A1 | 5/2015 | Allen et al. |
| 2015/0148785 A1 | 5/2015 | Kleiner |
| 2015/0174304 A1 | 6/2015 | Askem et al. |
| 2015/0245949 A1 | 9/2015 | Locke et al. |
| 2015/0246164 A1 | 9/2015 | Heaton et al. |
| 2015/0250979 A1 | 9/2015 | Loske |
| 2015/0265741 A1 | 9/2015 | Duncan et al. |
| 2015/0265743 A1 | 9/2015 | Hanson et al. |
| 2015/0320901 A1 | 11/2015 | Chandrashekhar-Bhat et al. |
| 2016/0008293 A1 | 1/2016 | Shi et al. |
| 2016/0038626 A1 | 2/2016 | Locke et al. |
| 2016/0051724 A1 | 2/2016 | Sahin et al. |
| 2016/0067107 A1 | 3/2016 | Cotton |
| 2016/0100987 A1 | 4/2016 | Hartwell et al. |
| 2016/0106878 A1 | 4/2016 | Yang et al. |
| 2016/0106892 A1 | 4/2016 | Hartwell |
| 2016/0114281 A1* | 4/2016 | Bonano .............. B01D 53/0446 96/131 |
| 2016/0166422 A1 | 6/2016 | Karim et al. |
| 2016/0193244 A1 | 7/2016 | Ota et al. |
| 2016/0222548 A1 | 8/2016 | Agboh |
| 2016/0271178 A1 | 9/2016 | Hauser et al. |
| 2016/0287743 A1 | 10/2016 | Andrews |

(56) References Cited

U.S. PATENT DOCUMENTS

| | | |
|---|---|---|
| 2016/0339158 A1 | 11/2016 | Collinson et al. |
| 2016/0374847 A1 | 12/2016 | Lachenbruch et al. |
| 2017/0014275 A1 | 1/2017 | Schneider |
| 2017/0049111 A1 | 2/2017 | Patton et al. |
| 2017/0072669 A1 | 3/2017 | Sekido et al. |
| 2017/0128269 A1 | 5/2017 | Coulthard et al. |
| 2017/0189237 A1 | 7/2017 | Locke et al. |
| 2017/0189575 A1 | 7/2017 | Lee et al. |
| 2017/0209615 A1 | 7/2017 | Tornero Garcia et al. |
| 2017/0232161 A1 | 8/2017 | Fewkes et al. |
| 2017/0258956 A1 | 9/2017 | Flach et al. |
| 2017/0367895 A1 | 12/2017 | Holm et al. |
| 2017/0368239 A1 | 12/2017 | Askem et al. |
| 2018/0008742 A1 | 1/2018 | Hoggarth et al. |
| 2018/0014974 A1 | 1/2018 | Hoggarth et al. |
| 2018/0023217 A1 | 1/2018 | Patton et al. |
| 2018/0030321 A1 | 2/2018 | Tunius |
| 2018/0042789 A1 | 2/2018 | Bradford et al. |
| 2018/0078423 A1 | 3/2018 | Magin et al. |
| 2018/0086903 A1 | 3/2018 | Zhang et al. |
| 2018/0118809 A1 | 5/2018 | Mearns Spragg |
| 2018/0133066 A1 | 5/2018 | Ahsani et al. |
| 2018/0140467 A1 | 5/2018 | Hunt |
| 2018/0140822 A1 | 5/2018 | Robinson et al. |
| 2018/0200414 A1 | 7/2018 | Askem et al. |
| 2018/0221531 A1 | 8/2018 | Bender et al. |
| 2018/0236124 A1 | 8/2018 | Young et al. |
| 2018/0243463 A1 | 8/2018 | Chatterjee et al. |
| 2018/0243464 A1 | 8/2018 | Hwang et al. |
| 2018/0244857 A1 | 8/2018 | Lee et al. |
| 2018/0272052 A1 | 9/2018 | Locke et al. |
| 2018/0296397 A1 | 10/2018 | Askem et al. |
| 2018/0303873 A1 | 10/2018 | Been et al. |
| 2018/0311419 A1 | 11/2018 | Locke et al. |
| 2018/0333522 A1 | 11/2018 | Pratt et al. |
| 2018/0344533 A1 | 12/2018 | Rovaniemi |
| 2018/0353334 A1 | 12/2018 | Locke et al. |
| 2018/0353337 A1 | 12/2018 | Locke |
| 2018/0353339 A1 | 12/2018 | Locke et al. |
| 2018/0353340 A1 | 12/2018 | Robinson et al. |
| 2018/0353344 A1 | 12/2018 | Locke et al. |
| 2018/0353662 A1 | 12/2018 | Locke et al. |
| 2018/0353663 A1 | 12/2018 | Locke et al. |
| 2018/0360667 A1 | 12/2018 | Droche |
| 2019/0000677 A1 | 1/2019 | Munro |
| 2019/0001030 A1* | 1/2019 | Braga ................ A61M 1/784 |
| 2019/0015258 A1 | 1/2019 | Gowans et al. |
| 2019/0015468 A1 | 1/2019 | Yadav et al. |
| 2019/0030223 A1* | 1/2019 | Lin ...................... A61M 3/02 |
| 2019/0046682 A1 | 2/2019 | Choi et al. |
| 2019/0060127 A1 | 2/2019 | Locke et al. |
| 2019/0083752 A1 | 3/2019 | Howell et al. |
| 2019/0117465 A1 | 4/2019 | Osborne et al. |
| 2019/0117466 A1 | 4/2019 | Kazala, Jr. et al. |
| 2019/0117861 A1 | 4/2019 | Locke et al. |
| 2019/0125590 A1 | 5/2019 | Rehbein et al. |
| 2019/0133830 A1 | 5/2019 | Bishop et al. |
| 2019/0151155 A1 | 5/2019 | Bonn |
| 2019/0151159 A1 | 5/2019 | Gowans et al. |
| 2019/0151495 A1 | 5/2019 | Helary et al. |
| 2019/0184052 A1 | 6/2019 | Ilan et al. |
| 2019/0231600 A1 | 8/2019 | Locke et al. |
| 2019/0231602 A1 | 8/2019 | Locke et al. |
| 2019/0231943 A1 | 8/2019 | Robinson et al. |
| 2019/0274889 A1 | 9/2019 | Steward et al. |
| 2019/0282728 A1 | 9/2019 | Kellar et al. |
| 2019/0290799 A1 | 9/2019 | Arshi et al. |
| 2019/0298249 A1 | 10/2019 | Bates et al. |
| 2019/0298577 A1 | 10/2019 | Locke et al. |
| 2019/0298578 A1 | 10/2019 | Shulman et al. |
| 2019/0298579 A1 | 10/2019 | Moore et al. |
| 2019/0298580 A1 | 10/2019 | Hall et al. |
| 2019/0298582 A1 | 10/2019 | Addison et al. |
| 2019/0298881 A1 | 10/2019 | Ramjit et al. |
| 2019/0298882 A1 | 10/2019 | Nelson |
| 2019/0298895 A1 | 10/2019 | Selby et al. |
| 2019/0307611 A1 | 10/2019 | Askem et al. |
| 2019/0307612 A1 | 10/2019 | Hartwell et al. |
| 2019/0307934 A1 | 10/2019 | Allen et al. |
| 2019/0307935 A1 | 10/2019 | Simmons et al. |
| 2019/0314187 A1 | 10/2019 | Emslander et al. |
| 2019/0314209 A1 | 10/2019 | Ha et al. |
| 2019/0314544 A1 | 10/2019 | Filho et al. |
| 2019/0321232 A1 | 10/2019 | Jardret et al. |
| 2019/0321509 A1 | 10/2019 | Chakravarthy et al. |
| 2019/0321526 A1 | 10/2019 | Robinson et al. |
| 2019/0322795 A1 | 10/2019 | Kubo et al. |
| 2019/0328580 A1 | 10/2019 | Emslander et al. |
| 2019/0336343 A1 | 11/2019 | Etchells et al. |
| 2019/0336344 A1 | 11/2019 | Locke |
| 2019/0336345 A1 | 11/2019 | Bannwart |
| 2019/0336346 A1 | 11/2019 | Locke et al. |
| 2019/0336640 A1 | 11/2019 | Vismara et al. |
| 2019/0336641 A1 | 11/2019 | Nisbet |
| 2019/0336643 A1 | 11/2019 | Luukko et al. |
| 2019/0336658 A1 | 11/2019 | Heaton et al. |
| 2019/0336739 A1 | 11/2019 | Locke et al. |
| 2019/0343687 A1 | 11/2019 | Locke et al. |
| 2019/0343889 A1 | 11/2019 | Luukko et al. |
| 2019/0343979 A1 | 11/2019 | Kearney et al. |
| 2019/0343993 A1 | 11/2019 | Weston |
| 2019/0343994 A1 | 11/2019 | Greener |
| 2019/0344242 A1 | 11/2019 | Kim et al. |
| 2019/0350763 A1 | 11/2019 | Pratt et al. |
| 2019/0350764 A1 | 11/2019 | Zochowski et al. |
| 2019/0350765 A1 | 11/2019 | Heagle et al. |
| 2019/0350775 A1 | 11/2019 | Biasutti et al. |
| 2019/0350970 A1 | 11/2019 | Saphier et al. |
| 2019/0351092 A1 | 11/2019 | Silver et al. |
| 2019/0351093 A1 | 11/2019 | Stein et al. |
| 2019/0351094 A1 | 11/2019 | Maher et al. |
| 2019/0351095 A1 | 11/2019 | Maher et al. |
| 2019/0351111 A1 | 11/2019 | Locke et al. |
| 2019/0358088 A1 | 11/2019 | Lavocah et al. |
| 2019/0358361 A1 | 11/2019 | McInnes et al. |
| 2019/0358372 A1 | 11/2019 | Askem et al. |
| 2019/0365948 A1 | 12/2019 | Deegan et al. |
| 2019/0365962 A1 | 12/2019 | Lee et al. |
| 2019/0374408 A1 | 12/2019 | Robles et al. |
| 2019/0374673 A1 | 12/2019 | Hoefinghoff et al. |
| 2019/0380878 A1 | 12/2019 | Edwards et al. |
| 2019/0380881 A1 | 12/2019 | Albert et al. |
| 2019/0380882 A1 | 12/2019 | Taylor et al. |
| 2019/0380883 A1 | 12/2019 | Macphee et al. |
| 2019/0381222 A9 | 12/2019 | Locke et al. |
| 2019/0388577 A1 | 12/2019 | Chandrashekhar-Bhat et al. |
| 2019/0388579 A1 | 12/2019 | Macphee et al. |
| 2019/0388589 A1 | 12/2019 | Macphee et al. |
| 2020/0000640 A1 | 1/2020 | Mondal et al. |
| 2020/0000642 A1 | 1/2020 | Waite |
| 2020/0000643 A1 | 1/2020 | Locke |
| 2020/0000955 A1 | 1/2020 | Andrews et al. |
| 2020/0000956 A1 | 1/2020 | Huang et al. |
| 2020/0000960 A1 | 1/2020 | Kellar et al. |
| 2020/0000985 A1 | 1/2020 | Seddon et al. |
| 2020/0008981 A1 | 1/2020 | Wheldrake |
| 2020/0009289 A1 | 1/2020 | Torabinejad et al. |
| 2020/0009400 A1 | 1/2020 | Ribeiro et al. |
| 2020/0017650 A1 | 1/2020 | Young et al. |
| 2020/0022844 A1 | 1/2020 | Blott et al. |
| 2020/0023102 A1 | 1/2020 | Powell |
| 2020/0023103 A1 | 1/2020 | Joshi et al. |
| 2020/0023104 A1 | 1/2020 | Eriksson et al. |
| 2020/0023105 A1 | 1/2020 | Long et al. |
| 2020/0023106 A1 | 1/2020 | Carroll et al. |
| 2020/0030153 A1 | 1/2020 | Johannison et al. |
| 2020/0030480 A1 | 1/2020 | Choi |
| 2020/0030499 A1 | 1/2020 | Menon et al. |
| 2020/0038023 A1 | 2/2020 | Dunn |
| 2020/0038249 A1 | 2/2020 | Pratt et al. |
| 2020/0038250 A1 | 2/2020 | Edwards et al. |
| 2020/0038251 A1 | 2/2020 | Locke et al. |
| 2020/0038252 A1 | 2/2020 | Spiro |
| 2020/0038283 A1 | 2/2020 | Hall et al. |

(56) References Cited

U.S. PATENT DOCUMENTS

| | | |
|---|---|---|
| 2020/0038470 A1 | 2/2020 | Datt et al. |
| 2020/0038544 A1 | 2/2020 | Grover et al. |
| 2020/0038546 A1 | 2/2020 | Dizio et al. |
| 2020/0038639 A1 | 2/2020 | Patel et al. |
| 2020/0046565 A1 | 2/2020 | Barta et al. |
| 2020/0046566 A1 | 2/2020 | Carey et al. |
| 2020/0046567 A1 | 2/2020 | Carroll et al. |
| 2020/0046568 A1 | 2/2020 | Sexton |
| 2020/0046663 A1 | 2/2020 | Murdock et al. |
| 2020/0046876 A1 | 2/2020 | Liu |
| 2020/0046887 A1 | 2/2020 | Runquist et al. |
| 2020/0054491 A1 | 2/2020 | Hentrich et al. |
| 2020/0054781 A1 | 2/2020 | Weiser et al. |
| 2020/0060879 A1 | 2/2020 | Edwards et al. |
| 2020/0061253 A1 | 2/2020 | Long et al. |
| 2020/0061254 A1 | 2/2020 | Joshi et al. |
| 2020/0061379 A1 | 2/2020 | Bogie et al. |
| 2020/0069183 A1 | 3/2020 | Rice et al. |
| 2020/0069476 A1 | 3/2020 | Randolph et al. |
| 2020/0069477 A1 | 3/2020 | Holm et al. |
| 2020/0069478 A1 | 3/2020 | Jabbarzadeh et al. |
| 2020/0069479 A1 | 3/2020 | Buan et al. |
| 2020/0069835 A1 | 3/2020 | Hissink et al. |
| 2020/0069850 A1 | 3/2020 | Beadle et al. |
| 2020/0069851 A1 | 3/2020 | Blott et al. |
| 2020/0069853 A1 | 3/2020 | Hall et al. |
| 2020/0078223 A1 | 3/2020 | Locke et al. |
| 2020/0078224 A1 | 3/2020 | Carroll et al. |
| 2020/0078225 A1 | 3/2020 | Grillitsch et al. |
| 2020/0078305 A1 | 3/2020 | Auvinen et al. |
| 2020/0078330 A1 | 3/2020 | Gay |
| 2020/0078482 A1 | 3/2020 | Yoon et al. |
| 2020/0078499 A1 | 3/2020 | Gadde et al. |
| 2020/0085625 A1 | 3/2020 | Bellini et al. |
| 2020/0085626 A1 | 3/2020 | Braga et al. |
| 2020/0085629 A1 | 3/2020 | Locke et al. |
| 2020/0085630 A1 | 3/2020 | Robinson et al. |
| 2020/0085632 A1 | 3/2020 | Locke et al. |
| 2020/0085991 A1 | 3/2020 | Coomber |
| 2020/0085992 A1 | 3/2020 | Locke et al. |
| 2020/0086014 A1 | 3/2020 | Locke et al. |
| 2020/0086017 A1 | 3/2020 | Jardret et al. |
| 2020/0086049 A1 | 3/2020 | Park et al. |
| 2020/0093646 A1 | 3/2020 | Locke et al. |
| 2020/0093756 A1 | 3/2020 | Sabacinski |
| 2020/0093953 A1 | 3/2020 | Kim et al. |
| 2020/0093954 A1 | 3/2020 | Leise, III |
| 2020/0093970 A1 | 3/2020 | Hunt et al. |
| 2020/0095421 A1 | 3/2020 | Kettel |
| 2020/0100945 A1 | 4/2020 | Albert et al. |
| 2020/0101192 A1 | 4/2020 | Folwarzny |
| 2020/0107964 A1 | 4/2020 | Locke et al. |
| 2020/0107965 A1 | 4/2020 | Greener |
| 2020/0107966 A1 | 4/2020 | Francis |
| 2020/0107967 A1 | 4/2020 | Holm et al. |
| 2020/0108169 A1 | 4/2020 | Hu et al. |
| 2020/0113741 A1 | 4/2020 | Rehbein et al. |
| 2020/0114039 A1 | 4/2020 | Wang et al. |
| 2020/0114040 A1 | 4/2020 | Waite et al. |
| 2020/0114049 A1 | 4/2020 | Wall |
| 2020/0121509 A1 | 4/2020 | Locke et al. |
| 2020/0121510 A1 | 4/2020 | Hartwell et al. |
| 2020/0121513 A1 | 4/2020 | Townsend et al. |
| 2020/0121521 A1 | 4/2020 | Daniel et al. |
| 2020/0121833 A9 | 4/2020 | Askem et al. |
| 2020/0129338 A1 | 4/2020 | Gardiner et al. |
| 2020/0129341 A1 | 4/2020 | Coulthard et al. |
| 2020/0129648 A1 | 4/2020 | Drury et al. |
| 2020/0129654 A1 | 4/2020 | Bouvier et al. |
| 2020/0129655 A1 | 4/2020 | Gardiner et al. |
| 2020/0129675 A1 | 4/2020 | Robinson et al. |
| 2020/0138754 A1 | 5/2020 | Johnson |
| 2020/0139002 A1 | 5/2020 | Dudnyk et al. |
| 2020/0139023 A1 | 5/2020 | Haggstrom et al. |
| 2020/0139025 A1 | 5/2020 | Robinson et al. |
| 2020/0141031 A1 | 5/2020 | Kosan et al. |
| 2020/0146894 A1 | 5/2020 | Long et al. |
| 2020/0146896 A1 | 5/2020 | Rice et al. |
| 2020/0146897 A1 | 5/2020 | Locke et al. |
| 2020/0146899 A1 | 5/2020 | Pratt et al. |
| 2020/0155355 A1 | 5/2020 | Hill et al. |
| 2020/0155358 A1 | 5/2020 | Wheldrake |
| 2020/0155359 A1 | 5/2020 | Carroll et al. |
| 2020/0155361 A1 | 5/2020 | Pigg et al. |
| 2020/0155379 A1 | 5/2020 | Shaw et al. |
| 2020/0163802 A1 | 5/2020 | Hunt et al. |
| 2020/0163803 A1 | 5/2020 | Pigg et al. |
| 2020/0164112 A1 | 5/2020 | Kato et al. |
| 2020/0164120 A1 | 5/2020 | Jaecklein et al. |
| 2020/0170841 A1 | 6/2020 | Waite et al. |
| 2020/0170842 A1 | 6/2020 | Locke |
| 2020/0170843 A1 | 6/2020 | Collinson et al. |
| 2020/0171197 A1 | 6/2020 | Hubbell et al. |
| 2020/0179300 A1 | 6/2020 | Urban et al. |
| 2020/0179558 A1 | 6/2020 | Munro et al. |
| 2020/0179673 A1 | 6/2020 | Wan |
| 2020/0188179 A1 | 6/2020 | Bugedo-Albizuri et al. |
| 2020/0188180 A1 | 6/2020 | Akbari et al. |
| 2020/0188182 A1 | 6/2020 | Sanders et al. |
| 2020/0188183 A1 | 6/2020 | Hamerslagh et al. |
| 2020/0188550 A1 | 6/2020 | Dagger et al. |
| 2020/0188564 A1 | 6/2020 | Dunn |
| 2020/0190310 A1 | 6/2020 | Meyer |
| 2020/0197227 A1 | 6/2020 | Locke et al. |
| 2020/0197228 A1 | 6/2020 | Hartwell |
| 2020/0197559 A1 | 6/2020 | Bourdillon et al. |
| 2020/0197580 A1 | 6/2020 | Kilpadi et al. |
| 2020/0206035 A1 | 7/2020 | Kantor et al. |
| 2020/0206036 A1 | 7/2020 | Robinson et al. |
| 2020/0214637 A1 | 7/2020 | Brownhill et al. |
| 2020/0214897 A1 | 7/2020 | Long et al. |
| 2020/0214898 A1 | 7/2020 | Waite et al. |
| 2020/0214899 A1 | 7/2020 | Locke et al. |
| 2020/0215220 A1 | 7/2020 | Schomburg et al. |
| 2020/0215226 A1 | 7/2020 | Kitagawa et al. |
| 2020/0222469 A1 | 7/2020 | Cotton |
| 2020/0229983 A1 | 7/2020 | Robinson et al. |
| 2020/0230283 A1 | 7/2020 | Yang et al. |
| 2020/0237562 A1 | 7/2020 | Rice et al. |
| 2020/0237564 A1 | 7/2020 | Hammond et al. |
| 2020/0237816 A1 | 7/2020 | Lait |
| 2020/0246190 A1 | 8/2020 | Luckemeyer et al. |
| 2020/0246191 A1 | 8/2020 | Lu et al. |
| 2020/0246194 A1 | 8/2020 | Gonzalez et al. |
| 2020/0246195 A1 | 8/2020 | Robinson et al. |
| 2020/0253785 A1 | 8/2020 | Bernet et al. |
| 2020/0253786 A1 | 8/2020 | Harrison et al. |
| 2020/0253788 A1 | 8/2020 | Rehbein et al. |
| 2020/0254139 A1 | 8/2020 | Phillips et al. |
| 2020/0261275 A1 | 8/2020 | Manwaring et al. |
| 2020/0261276 A1 | 8/2020 | Lujan Hernandez et al. |
| 2020/0268560 A1 | 8/2020 | Harrison et al. |
| 2020/0268561 A1 | 8/2020 | Locke et al. |
| 2020/0269028 A1 | 8/2020 | Hegg |
| 2020/0270484 A1 | 8/2020 | Lipscomb et al. |
| 2020/0276055 A1 | 9/2020 | Randolph et al. |
| 2020/0276058 A1 | 9/2020 | Locke et al. |
| 2020/0277450 A1 | 9/2020 | Silverstein et al. |
| 2020/0281519 A1 | 9/2020 | Gowans et al. |
| 2020/0281529 A1 | 9/2020 | Grubb et al. |
| 2020/0281678 A1 | 9/2020 | Long et al. |
| 2020/0281775 A1 | 9/2020 | Kushnir et al. |
| 2020/0282100 A1 | 9/2020 | Gil et al. |
| 2020/0282114 A1 | 9/2020 | Long et al. |
| 2020/0282115 A1 | 9/2020 | Gardner et al. |
| 2020/0289326 A1 | 9/2020 | Nielsen et al. |
| 2020/0289327 A1 | 9/2020 | Hansen et al. |
| 2020/0289328 A1 | 9/2020 | Luckemeyer et al. |
| 2020/0289346 A1 | 9/2020 | Hansen et al. |
| 2020/0289347 A1 | 9/2020 | Gowans et al. |
| 2020/0289701 A1 | 9/2020 | Hall et al. |
| 2020/0289712 A1 | 9/2020 | Jiang et al. |
| 2020/0289723 A1 | 9/2020 | Gregory et al. |
| 2020/0289726 A1 | 9/2020 | Locke et al. |

(56) References Cited

U.S. PATENT DOCUMENTS

| | | |
|---|---|---|
| 2020/0289727 A1 | 9/2020 | Locke |
| 2020/0289806 A1 | 9/2020 | Locke et al. |
| 2020/0297541 A1 | 9/2020 | Hartwell et al. |
| 2020/0297543 A1 | 9/2020 | Rodzewicz et al. |
| 2020/0297544 A1 | 9/2020 | Moine et al. |
| 2020/0297892 A1 | 9/2020 | Silcock |
| 2020/0297893 A1 | 9/2020 | Ericson |
| 2020/0297894 A1 | 9/2020 | Koyama et al. |
| 2020/0299865 A1 | 9/2020 | Bonnefin et al. |
| 2020/0306089 A1 | 10/2020 | Delury et al. |
| 2020/0306091 A1 | 10/2020 | Lee et al. |
| 2020/0306092 A1 | 10/2020 | Rehbein et al. |
| 2020/0306094 A1 | 10/2020 | Kushnir et al. |
| 2020/0306426 A1 | 10/2020 | Rice et al. |
| 2020/0306428 A1 | 10/2020 | Ingram et al. |
| 2020/0306430 A1 | 10/2020 | Rehbein et al. |
| 2020/0315853 A1 | 10/2020 | Waite |
| 2020/0315854 A1 | 10/2020 | Simmons et al. |
| 2020/0315894 A1 | 10/2020 | Churilla et al. |
| 2020/0316271 A1 | 10/2020 | Lin |
| 2020/0316272 A1 | 10/2020 | Simpson |
| 2020/0316273 A1 | 10/2020 | Hegg |
| 2020/0323692 A1 | 10/2020 | Locke et al. |
| 2020/0324015 A1 | 10/2020 | Kettel et al. |
| 2020/0330283 A1 | 10/2020 | Locke et al. |
| 2020/0330284 A1 | 10/2020 | Locke et al. |
| 2020/0330285 A1 | 10/2020 | Rehbein et al. |
| 2020/0330658 A1 | 10/2020 | Fujisaki |
| 2020/0330660 A1 | 10/2020 | Patel et al. |
| 2020/0337719 A1 | 10/2020 | Ingram et al. |
| 2020/0337904 A1 | 10/2020 | Waite |
| 2020/0337905 A1 | 10/2020 | Earl et al. |
| 2020/0337906 A1 | 10/2020 | Long et al. |
| 2020/0337908 A1 | 10/2020 | Long et al. |
| 2020/0338228 A1 | 10/2020 | Kharkar et al. |
| 2020/0338243 A1 | 10/2020 | Harrison et al. |
| 2021/0170066 A1 | 6/2021 | Buan et al. |
| 2021/0187171 A1 | 6/2021 | Collinson et al. |
| 2021/0187174 A1 | 6/2021 | Locke |
| 2021/0196868 A1 | 7/2021 | Robinson et al. |
| 2021/0236342 A1 | 8/2021 | Long et al. |
| 2021/0252208 A1 | 8/2021 | Childress et al. |
| 2021/0275736 A1 | 9/2021 | Locke et al. |
| 2021/0290837 A1 | 9/2021 | Brandolini et al. |
| 2021/0322666 A1 | 10/2021 | Greener |
| 2021/0330956 A1 | 10/2021 | Robinson et al. |
| 2021/0338486 A1 | 11/2021 | Dagger et al. |
| 2021/0338487 A1 | 11/2021 | Robinson et al. |
| 2021/0353470 A1 | 11/2021 | Donda et al. |
| 2021/0361852 A1 | 11/2021 | Locke et al. |
| 2021/0361854 A1 | 11/2021 | Askem et al. |
| 2021/0370043 A1 | 12/2021 | Luckemeyer et al. |
| 2021/0378876 A1 | 12/2021 | Gowans |
| 2021/0379273 A1 | 12/2021 | Locke et al. |
| 2022/0000670 A1 | 1/2022 | Adie et al. |
| 2022/0000672 A1 | 1/2022 | Hunt |
| 2022/0001094 A1 | 1/2022 | Pratt et al. |
| 2022/0001095 A1 | 1/2022 | Locke et al. |
| 2022/0001096 A1 | 1/2022 | Locke et al. |
| 2022/0001101 A1 | 1/2022 | Hunt et al. |
| 2022/0001212 A1 | 1/2022 | Bass et al. |
| 2022/0002916 A1 | 1/2022 | Wheldrake |
| 2022/0008642 A1 | 1/2022 | Waite et al. |
| 2022/0016331 A1 | 1/2022 | Robinson et al. |
| 2022/0016332 A1 | 1/2022 | Joshi et al. |
| 2022/0023103 A1 | 1/2022 | Locke et al. |
| 2022/0023527 A1 | 1/2022 | Beadle et al. |
| 2022/0031231 A1 | 2/2022 | Hunt et al. |
| 2022/0031934 A1 | 2/2022 | Locke et al. |
| 2022/0047797 A1 | 2/2022 | Locke et al. |
| 2022/0062060 A1 | 3/2022 | Hu et al. |
| 2022/0062526 A1 | 3/2022 | Heaton et al. |
| 2022/0080102 A1 | 3/2022 | Locke et al. |
| 2022/0080103 A1 | 3/2022 | Locke et al. |
| 2022/0096727 A1 | 3/2022 | Collinson et al. |
| 2022/0117795 A1 | 4/2022 | Adie et al. |
| 2022/0117796 A1 | 4/2022 | Adie et al. |
| 2022/0117797 A1 | 4/2022 | Adie et al. |
| 2022/0183894 A1 | 6/2022 | Mumby et al. |
| 2022/0192887 A1 | 6/2022 | Jardret et al. |
| 2022/0193324 A1 | 6/2022 | Locke et al. |
| 2024/0001020 A1 | 1/2024 | Walton et al. |
| 2024/0009372 A1 | 1/2024 | Braga et al. |
| 2024/0024561 A1 | 1/2024 | Locke et al. |
| 2024/0058176 A1 | 2/2024 | Beadle et al. |
| 2024/0074907 A1 | 3/2024 | Eriksson et al. |
| 2024/0074909 A1 | 3/2024 | Rapp |
| 2024/0080969 A1 | 3/2024 | Askem et al. |
| 2024/0099894 A1 | 3/2024 | Hartwell et al. |
| 2024/0099897 A1 | 3/2024 | Locke et al. |
| 2024/0100238 A1 | 3/2024 | Gordon et al. |
| 2024/0115789 A1 | 4/2024 | Locke et al. |
| 2024/0115797 A1 | 4/2024 | Luckemeyer et al. |
| 2024/0122764 A1 | 4/2024 | Hunt et al. |
| 2024/0148560 A1 | 5/2024 | Coulthard et al. |
| 2024/0156645 A1 | 5/2024 | Braga et al. |
| 2024/0189492 A1 | 6/2024 | Gowans et al. |
| 2024/0197538 A1 | 6/2024 | Cole et al. |
| 2024/0207102 A1 | 6/2024 | Allen et al. |

FOREIGN PATENT DOCUMENTS

| | | |
|---|---|---|
| EP | 3569260 A1 | 11/2019 |
| EP | 3622975 A1 | 3/2020 |
| EP | 3643328 A1 | 4/2020 |
| EP | 3643330 A1 | 4/2020 |
| EP | 3643331 A1 | 4/2020 |
| EP | 3669838 A1 | 6/2020 |
| EP | 3669843 A1 | 6/2020 |
| EP | 3669844 A1 | 6/2020 |
| EP | 3827795 A1 | 6/2021 |
| EP | 3829515 A1 | 6/2021 |
| EP | 3829667 A1 | 6/2021 |
| EP | 3347068 B1 | 7/2021 |
| EP | 3441051 B1 | 7/2021 |
| EP | 3851134 A1 | 7/2021 |
| EP | 3852827 A1 | 7/2021 |
| EP | 3852829 A1 | 7/2021 |
| EP | 3606573 B1 | 8/2021 |
| EP | 3866737 A1 | 8/2021 |
| EP | 3866920 A1 | 8/2021 |
| EP | 3291849 B1 | 9/2021 |
| EP | 3880143 A1 | 9/2021 |
| EP | 3880267 A1 | 9/2021 |
| EP | 3897489 A1 | 10/2021 |
| EP | 3060181 B1 | 11/2021 |
| EP | 3434237 B1 | 11/2021 |
| EP | 3624741 B1 | 11/2021 |
| EP | 3628289 B1 | 11/2021 |
| EP | 3104816 B1 | 12/2021 |
| EP | 3322455 B1 | 12/2021 |
| EP | 3429521 B1 | 12/2021 |
| EP | 3446665 B1 | 12/2021 |
| EP | 3681452 B1 | 12/2021 |
| EP | 3932442 A1 | 1/2022 |
| EP | 3936163 A1 | 1/2022 |
| EP | 3939554 A1 | 1/2022 |
| EP | 3124062 B1 | 2/2022 |
| EP | 3687467 B1 | 2/2022 |
| EP | 3481360 B1 | 3/2022 |
| EP | 3740179 B1 | 3/2022 |
| EP | 3964185 A1 | 3/2022 |
| EP | 3454807 B1 | 4/2022 |
| EP | 3421020 B1 | 5/2022 |
| EP | 3871645 B1 | 5/2022 |
| EP | 3452132 B1 | 1/2024 |
| EP | 3592312 B1 | 1/2024 |
| EP | 3677291 B1 | 1/2024 |
| EP | 3769791 B1 | 1/2024 |
| EP | 3656408 B1 | 2/2024 |
| EP | 3659409 B1 | 2/2024 |
| EP | 3651815 B1 | 3/2024 |
| EP | 2767305 B2 | 4/2024 |
| EP | 3503857 B1 | 4/2024 |

(56) References Cited

FOREIGN PATENT DOCUMENTS

| | | |
|---|---|---|
| EP | 3703632 B1 | 4/2024 |
| EP | 3936163 B1 | 4/2024 |
| EP | 4346340 A2 | 4/2024 |
| EP | 4353271 A1 | 4/2024 |
| EP | 3292878 B1 | 5/2024 |
| EP | 3708197 B1 | 5/2024 |
| EP | 2253353 B2 | 6/2024 |
| EP | 3291849 B2 | 6/2024 |
| EP | 3470030 B1 | 6/2024 |
| EP | 3785744 B1 | 6/2024 |
| GB | 2579211 A | 6/2020 |
| GB | 2579368 A | 6/2020 |
| GB | 2589503 B | 6/2021 |
| GB | 2592804 A | 9/2021 |
| GB | 2592805 A | 9/2021 |
| GB | 2592806 A | 9/2021 |
| WO | 2005018543 A2 | 3/2005 |
| WO | 2011121394 A1 | 10/2011 |
| WO | 2011135284 A1 | 11/2011 |
| WO | 2011144888 A1 | 11/2011 |
| WO | 2013015827 A2 | 1/2013 |
| WO | 2013126049 A1 | 8/2013 |
| WO | 2014014842 A1 | 1/2014 |
| WO | 2015145117 A1 | 10/2015 |
| WO | 2015173546 A1 | 11/2015 |
| WO | 2016141450 A1 | 9/2016 |
| WO | 2017016974 A1 | 2/2017 |
| WO | 2017125250 A1 | 7/2017 |
| WO | 2018029231 A1 | 2/2018 |
| WO | 2018094061 A1 | 5/2018 |
| WO | 2018162613 A1 | 9/2018 |
| WO | 2018163093 A1 | 9/2018 |
| WO | 2018189265 A1 | 10/2018 |
| WO | 2018226667 A1 | 12/2018 |
| WO | 2018227144 A1 | 12/2018 |
| WO | 2018231825 A1 | 12/2018 |
| WO | 2018236648 A1 | 12/2018 |
| WO | 2019002085 A1 | 1/2019 |
| WO | 2019012068 A1 | 1/2019 |
| WO | 2019012069 A1 | 1/2019 |
| WO | 2019022493 A1 | 1/2019 |
| WO | 2019027933 A1 | 2/2019 |
| WO | 2019038548 A1 | 2/2019 |
| WO | 2019038549 A1 | 2/2019 |
| WO | 2019040656 A1 | 2/2019 |
| WO | 2019050855 A1 | 3/2019 |
| WO | 2019058373 A1 | 3/2019 |
| WO | 2019073326 A1 | 4/2019 |
| WO | 2019083563 A1 | 5/2019 |
| WO | 2019083868 A1 | 5/2019 |
| WO | 2019086911 A1 | 5/2019 |
| WO | 2019091150 A1 | 5/2019 |
| WO | 2019094147 A1 | 5/2019 |
| WO | 2019096828 A1 | 5/2019 |
| WO | 2019113275 A1 | 6/2019 |
| WO | 2019113623 A1 | 6/2019 |
| WO | 2019191590 A1 | 10/2019 |
| WO | 2019193141 A1 | 10/2019 |
| WO | 2019193333 A1 | 10/2019 |
| WO | 2019199389 A1 | 10/2019 |
| WO | 2019199596 A1 | 10/2019 |
| WO | 2019199687 A1 | 10/2019 |
| WO | 2019199798 A1 | 10/2019 |
| WO | 2019199849 A1 | 10/2019 |
| WO | 2019200035 A1 | 10/2019 |
| WO | 2019215572 A1 | 11/2019 |
| WO | 2019219613 A1 | 11/2019 |
| WO | 2019234365 A1 | 12/2019 |
| WO | 2020005062 A1 | 1/2020 |
| WO | 2020005344 A1 | 1/2020 |
| WO | 2020005536 A1 | 1/2020 |
| WO | 2020005546 A1 | 1/2020 |
| WO | 2020005577 A1 | 1/2020 |
| WO | 2020007429 A1 | 1/2020 |
| WO | 2020011691 A1 | 1/2020 |
| WO | 2020014178 A1 | 1/2020 |
| WO | 2020014310 A1 | 1/2020 |
| WO | 2020018300 A1 | 1/2020 |
| WO | 2020026061 A1 | 2/2020 |
| WO | 2020026144 A1 | 2/2020 |
| WO | 2020033351 A1 | 2/2020 |
| WO | 2020035811 A1 | 2/2020 |
| WO | 2020043665 A1 | 3/2020 |
| WO | 2020044237 A1 | 3/2020 |
| WO | 2020046443 A1 | 3/2020 |
| WO | 2020047255 A1 | 3/2020 |
| WO | 2020049038 A1 | 3/2020 |
| WO | 2020055945 A1 | 3/2020 |
| WO | 2020056014 A1 | 3/2020 |
| WO | 2020056182 A1 | 3/2020 |
| WO | 2020065531 A1 | 4/2020 |
| WO | 2020070231 A1 | 4/2020 |
| WO | 2020074512 A1 | 4/2020 |
| WO | 2020078993 A1 | 4/2020 |
| WO | 2020079009 A1 | 4/2020 |
| WO | 2020079330 A1 | 4/2020 |
| WO | 2020081259 A1 | 4/2020 |
| WO | 2020081391 A1 | 4/2020 |
| WO | 2020092598 A1 | 5/2020 |
| WO | 2020136555 A1 | 7/2020 |
| WO | 2020141059 A1 | 7/2020 |
| WO | 2020144347 A1 | 7/2020 |
| WO | 2020150548 A1 | 7/2020 |
| WO | 2020159675 A1 | 8/2020 |
| WO | 2020159677 A1 | 8/2020 |
| WO | 2020159678 A1 | 8/2020 |
| WO | 2020159823 A1 | 8/2020 |
| WO | 2020159859 A1 | 8/2020 |
| WO | 2020159892 A1 | 8/2020 |
| WO | 2020161086 A1 | 8/2020 |
| WO | 2020173665 A1 | 9/2020 |
| WO | 2020173760 A1 | 9/2020 |
| WO | 2020174264 A1 | 9/2020 |
| WO | 2020174510 A1 | 9/2020 |
| WO | 2020182887 A1 | 9/2020 |
| WO | 2020185810 A1 | 9/2020 |
| WO | 2020197759 A1 | 10/2020 |
| WO | 2020197760 A1 | 10/2020 |
| WO | 2020198484 A1 | 10/2020 |
| WO | 2020201879 A1 | 10/2020 |
| WO | 2020213998 A1 | 10/2020 |

\* cited by examiner

FLUID COLLECTION APPARATUS

CROSS-REFERENCE

This patent application is a U.S. national phase entry of international application no. PCT/IB2018/001417 filed Nov. 16, 2018; claims the benefit of GB1719014.1 filed Nov. 16, 2017; and GB1719027.3 filed Nov. 16, 2017; each of which is incorporated herein by reference in their entirety.

BACKGROUND

Exudating wounds may be treated by providing negative pressure to the space above the wound to promote healing in a process often referred to as negative pressure wound therapy (NPWT). During NPWT, effluent such as exudate is removed from the wound and collected. In some therapies, the effluent is stored in a fluid collection apparatus positioned between the source of negative pressure and a the wound site. Typically the apparatus has a specific orientation to prevent exudate drawn into the apparatus from reaching the air outlet of the collection apparatus or otherwise prevent excess exudate from being drawn into the collection apparatus and/or fluid or other undesirable material being drawn into the negative pressure supply. As a consequence of this specific orientation, the patient may be restricted in mobility. In addition, care must be taken so that the specific orientation is not disrupted, which can interrupt the NPWT process.

BRIEF SUMMARY OF THE INVENTION

In one aspect, disclosed herein is an apparatus configured to allow for orientation independence during negative pressure wound therapy (NPWT). For instance, an apparatus comprising multiple sides (e.g., six sides), may be positioned in such a way that any of the multiple sides may be laid against a horizontal or substantially horizontal surface in use. As a non-limiting example, the apparatus may be capable of operating upside down such as may occur if carried in a bag when mobile or otherwise supported or placed in that orientation. The apparatus may additionally or alternatively be hung to a drip stand or other suitable device or affixed to a wall by an attachment point located on any of the multiple sides. This orientation independence may be achieved, for example, by arranging a first impeding element at a first end of a first fluid pathway defined by a first fluid defining element, such as a chamber or tube, in fluid communication with a source of negative pressure, and a second impeding element at a second end of the first fluid pathway, such that during NPWT, air may be preferentially drawn through the impeding element and into the first fluid pathway while liquid flow is impeded. Preferably, the first end of the first fluid defining element and a first side of the apparatus are in substantially fluid tight communication. Preferably, the second side of the apparatus opposes the first side of the apparatus. In an exemplary embodiment, as the apparatus fills with liquid, liquid may be drawn through the impeding elements and into the fluid pathway. As a non-limiting example, the liquid is drawn through the impeding elements and into the fluid pathway when the apparatus reaches a full or nearly-full state. To hinder liquid from being drawn from the fluid pathway into the source of negative pressure, the fluid pathway may comprise an air permeable member positioned within the fluid pathway to separate liquid drawn into the fluid pathway from the source of negative pressure. In some embodiments, the air permeable member is a filter that impedes liquid and solid material from passing through the member. In some instances, liquid drawn into the fluid pathway may saturate the air permeable member or the air permeable member may reach a pre-defined saturation level, which may cause an undesired change to the intended negative pressure level. In some cases, this pressure change may be used to detect or sense that the apparatus may be in a full or nearly-full state, and cause generation of negative pressure to halt. Accordingly, liquid may be prevented from entering into the source of negative pressure through the chamber once the air permeable member is saturated or reaches a pre-defined saturation level. In other instances, undesirable material such as wound tissue or absorbent material within the apparatus may block or clog the air permeable member which may cause an undesired change to the intended negative pressure level. In some cases, this pressure change may be used to detect or sense that the apparatus may not be functioning properly, and cause generation of negative pressure to halt. In some cases, this negative pressure change may be due to both of the aforesaid conditions. In some instances, the apparatus comprises an optional aromatic cartridge that may prevent external release of noxious odors drawn into the apparatus. The apparatus may further include one or more optional supports, such as a web or anchor to further retain the impeding element or elements in the chamber.

In some embodiments, disclosed herein are devices for negative pressure wound therapy comprising a collection vessel, a first fluid defining member configured to be in fluid communication with a source of negative pressure, a first impeding element positioned at a first end of the first fluid defining member, a second impeding element positioned at a second end of the first fluid defining member, and a second fluid defining member defining a pathway for dispensing fluid drawn from a wound site of a patient during negative pressure wound therapy into a collection region of the collection vessel; and wherein the first impeding element impedes fluid dispensed within the collection region from entering a first end of the first fluid defining member and the source of negative pressure, and the second impeding element impedes fluid dispensed within the collection region from entering a second end of the first fluid defining member and the source of negative pressure.

In some embodiments, the first and/or second impeding element of the devices disclosed herein comprise foam, in some instances open cell foam, and in further instances the impeding elements comprise polyurethane, polyether, polyvinyl alcohol (PVA), or a combination thereof. In some embodiments, the foam is a reticulated polyurethane foam. In some embodiments, the first fluid defining member is configured to hold the first and the second impeding elements in place within the fluid collection apparatus. In some embodiments, the first fluid defining member has a circular cross-section and/or may comprise a polycarbonate material. In yet other embodiments, the inner diameter of the first fluid defining member is between about 13 and about 23 mm, and the outer diameter of the first fluid defining member is between about 17 mm and about 27 mm.

In yet other embodiments, the devices disclosed herein further comprises a filter positioned within the first fluid defining member. In some embodiments, the filter is a hydrophobic filter; alternatively the filter comprises a pore size of between about 0.2 micron to about 0.8 micron. In other embodiments, the filter comprises polyethersulfone (PES), polytetrafluorethylene (PTFE), cellulose acetate, or a cellulose nitrate membrane.

In yet other embodiments, the devices disclosed herein further comprises a carbon filter. In yet other embodiments, the carbon filter comprises from about 25 g/m2 to about 200 g/m2 of activated carbon.

In some embodiments, the second fluid defining member comprises an elastomer, plastic, polyvinyl chloride (PVC), silicone, ethylene propylene diene monomer (EPDM), Viton, or a combination thereof. In some embodiments, the devices disclosed herein further comprises an absorbent material; in other embodiments, the absorbent material comprises a superabsorbent material, a fibrous structure impregnated with the superabsorbent material, sodium polyacrylate and cellulose pulp in the form of a sheet material, or combinations thereof. In other embodiments, the absorbent material comprises one or more layers of absorbent material within the fluid collection apparatus. In other embodiments, the absorbent material is provided within a sachet. In yet other embodiments, the sachet is dissolvable. In yet other embodiments, the devices disclosed herein further comprises a first wicking layer. In still other embodiments, the first wicking layer is positioned between the first impeding element and the absorbent material. In still other embodiments, the second fluid defining member extends through the first impeding element and comprises an outlet end positioned adjacent to the first wicking layer to wick the dispensed fluid into the absorbent material. In yet other embodiments, the outlet end of the second fluid defining member is positioned within about 10-60 mm of the first wicking layer. In yet other embodiments, the devices disclosed herein further comprises a second wicking layer. In still other embodiments, the second wicking layer is positioned between the absorbent material and the second impeding element. In yet other embodiments, the devices disclosed herein are configured to hold up to about 900 ml of fluid, up to about 600 ml of fluid or up to 300 ml of fluid. In still other embodiments, the devices disclosed herein further comprises an extension element extending the second fluid defining member to an area adjacent to or within the collection region of the collection vessel. In still other embodiments, the devices disclosed herein further comprise a cover. In still other embodiments, the first impeding element and the second impeding element are configured such that when the collection region of the collection vessel is filled with liquid to at least about 25% capacity by volume and sealed, in all orientations of the apparatus at least one of the first and second ends of the first fluid defining member is not submerged in liquid. In still other embodiments, the first impeding element and the second impeding element are configured such that when the collection region of the collection vessel is filled with fluid to at least about 50% capacity by volume and sealed, in all orientations of the apparatus at least one of the first and second ends of the first fluid defining member is not submerged in liquid. In some cases, the liquid is water. In some cases, the liquid is a physiological saline solution. As a non-limiting example, the physiological saline solution is defined in EN13726-1 as Test solution A.

Also included herein are methods for performing negative pressure wound therapy with the fluid collection apparatus devices disclosed herein. In some embodiments, the fluid collection apparatus devices disclosed herein comprises six sides, and the fluid collection apparatus in use is configured to be: (a) positioned with any of the six sides against a horizontal surface, and/or (b) hung from an attachment point on any of the six sides.

Also disclosed herein are methods of collecting fluid from a wound site of a subject, the method comprising: a) providing: i) a wound dressing positioned over the wound site, ii) a source of negative pressure, and iii) a fluid collection apparatus comprising a first fluid defining member in fluid communication with the source of negative pressure, a first impeding element positioned at a first end of the first fluid defining member, a second impeding element positioned at a second end of the first fluid defining member, and a second fluid defining member in fluid communication with the wound dressing; wherein the second fluid defining member defines a pathway for dispensing fluid drawn from the wound site into a fluid collection region of the fluid collection apparatus; and b) applying a negative pressure from the source of negative pressure to the wound site via the fluid collection apparatus to draw fluid from the wound site, through the second fluid defining member, and into the fluid collection region of the fluid collection apparatus; wherein the fluid comprises liquid and air, and fluid is retained in the fluid collection region and air is drawn through the first impeding element and/or the second impeding element, into the interior of first fluid defining member, and towards the source of negative pressure.

In some embodiments, the the fluid collection apparatus of the methods disclosed herein comprises multiple sides, and the fluid collection apparatus in use is: (a) positionable with any of the sides against a horizontal surface and/or (b) hung from an attachment point on any of the sides. In some embodiments, the fluid collection apparatus is suspended from one or more attachment points on the fluid collection apparatus. In some embodiments, when the fluid collection region is full or nearly full of fluid and/or other material than air, and the fluid saturates the filter or the filter reaches a pre-defined saturation level, a pressure drop is generated or sensed to stop application of negative pressure. In some embodiments, up to about 900 ml of fluid, up to about 600 ml of fluid, or up to about 300 ml of fluid is retained in the fluid collection region.

Also disclosed herein are multi-orientation fluid collection apparatus devices for negative pressure wound therapy comprising: a) a collection vessel comprising a first side and a second opposing side, b) optionally, a cover connected to the first side of the collection vessel, c) a first fluid pathway in fluid communication with a source of negative pressure, the first fluid pathway positioned between: (i) a first impeding element positioned at an interior of the cover or interior of the first side of the collection vessel and a (ii) second impeding element positioned at an interior of the second side of the collection vessel, wherein the first impeding element and the cover or first side of the collection vessel are in substantially fluid tight communication, d) a filter positioned within the first fluid pathway and between the first impeding element and the second impeding element, and e) a second fluid pathway for introducing exudate into the collection vessel.

In some embodiments, the collection vessel of the devices disclosed herein comprises additional sides positioned between the first and second opposing sides, and the multi-orientation fluid collection apparatus in use is capable of being: (a) positioned with the first side, the second opposing side, or any of the additional sides against a horizontal surface, and/or (b) hung from an attachment point on the first side, the second opposing side, or any of the additional sides.

Also disclosed herein are multi-orientation fluid collection apparatus devices connected to a source of negative pressure for collecting wound exudate, the apparatus comprising a collection vessel; a first fluid pathway comprising a first and a second end with impeding elements at the first and second ends, said first fluid pathway and a first side of the apparatus in fluid tight or substantially fluid tight communication with the source of negative pressure; and a second fluid pathway for drawing fluid from a wound site into the apparatus. In some embodiments, in use said second fluid pathway and said wound site are in fluid tight or substantially fluid tight communication. In some embodiments, the devices comprise an air permeable member situated within the first fluid pathway. In some embodiments, the devices comprise a third fluid pathway situated within the first fluid pathway and in fluid communication with the air permeable member for receiving air from the air permeable member; said third fluid pathway within said first fluid pathway and a first side of the apparatus in fluid tight or substantially fluid tight communication and the third fluid pathway in fluid communication with the source of negative pressure. In some embodiments, the first fluid pathway is defined by a first fluid defining member. In some embodiments, the first fluid defining member is a chamber. In some embodiments, the second fluid defining member is a fluid inlet for receiving fluid from the wound site under negative pressure. In some embodiments, the air permeable member comprises one or more filters. In some embodiments, the filter comprises a hydrophobic filter. In some embodiments, the impeding elements comprise foam.

DETAILED DESCRIPTION OF THE INVENTION

Figure 1A:
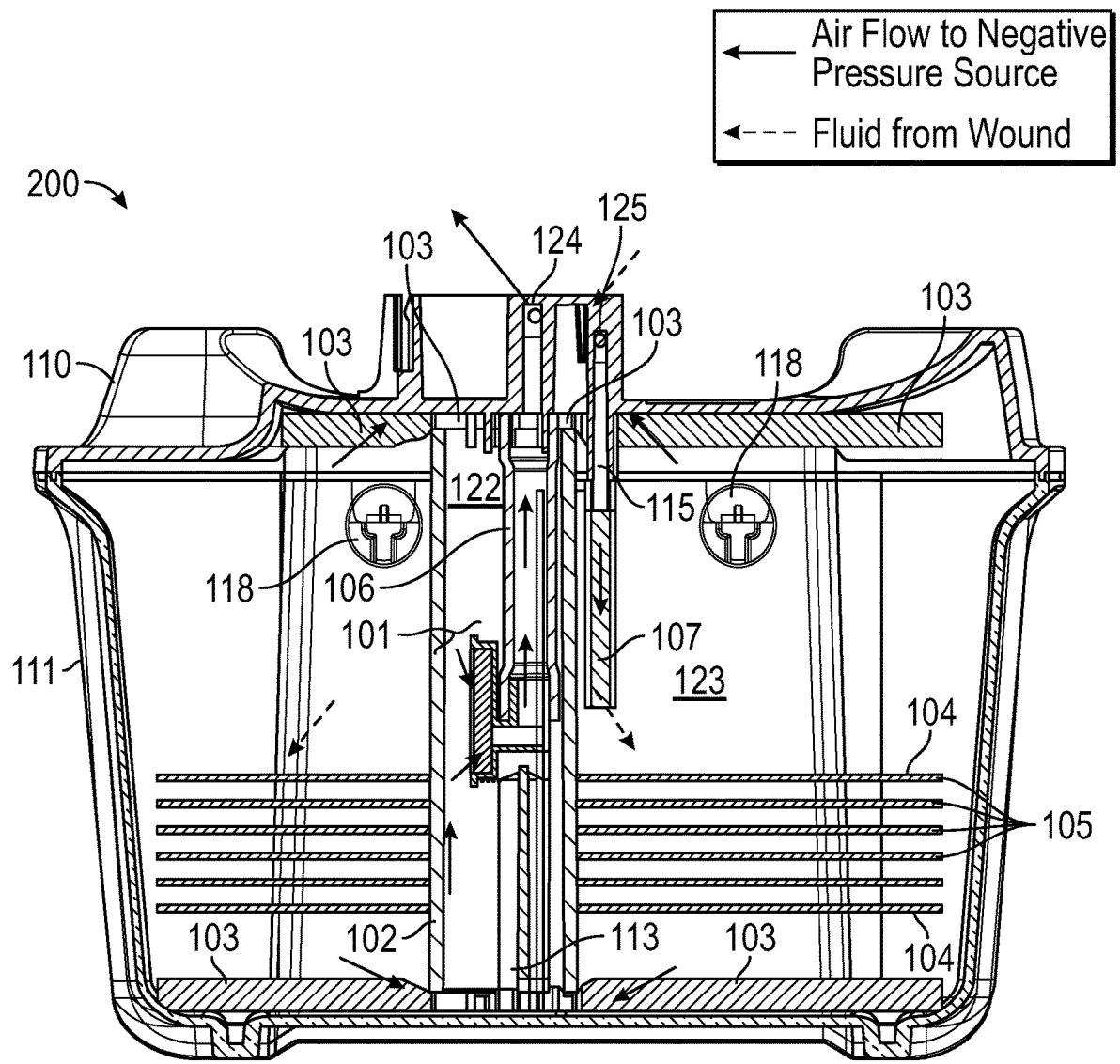
FIG. 1A depicts a front view of a first embodiment of a fluid collection apparatus.
Figure 1B:
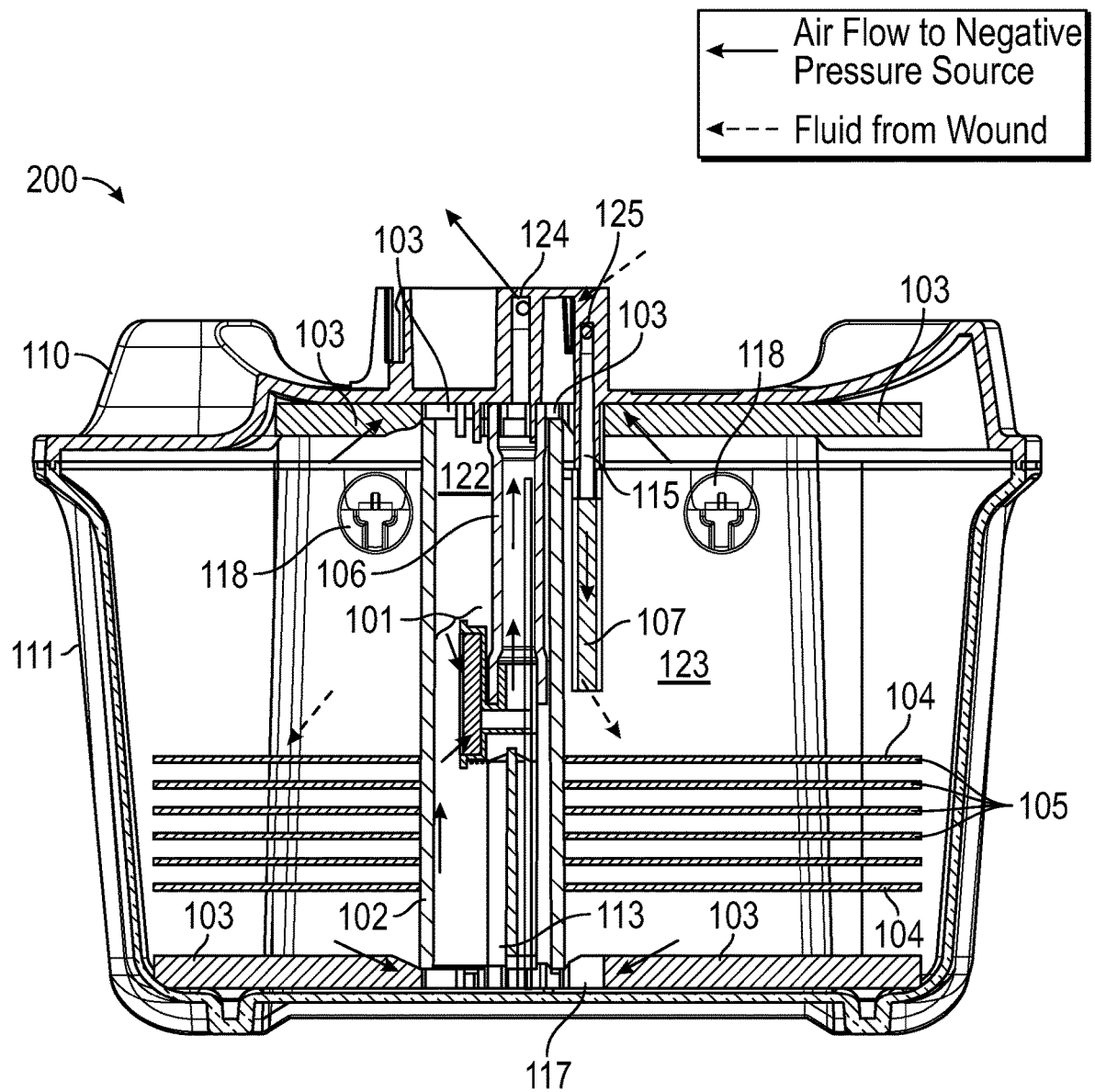
FIG. 1B depicts a front view of a second embodiment of a fluid collection apparatus.
Figure 4:
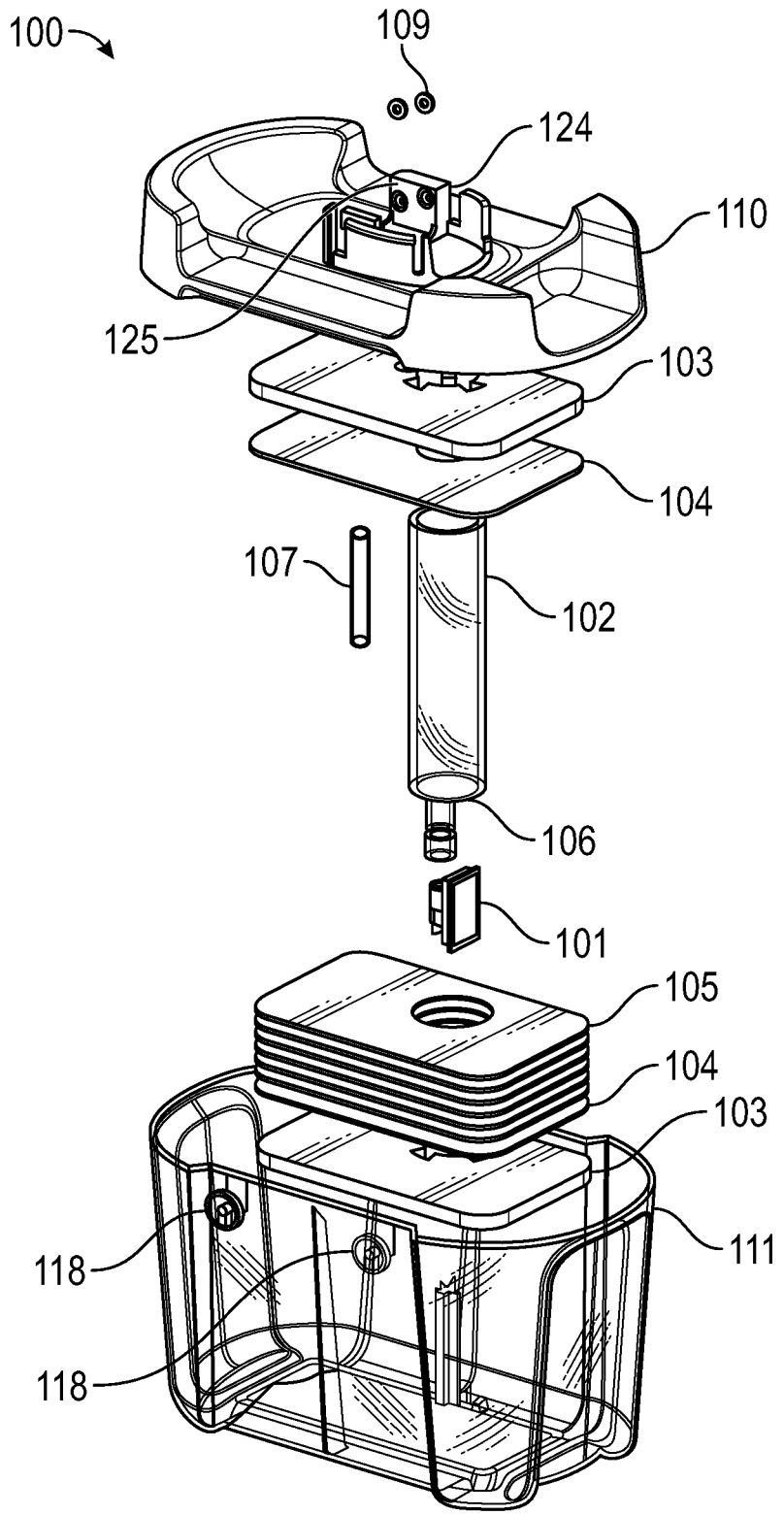
FIG. 4 depicts an exploded view of the first embodiment of the fluid collection apparatus.

In one aspect, provided herein are fluid collection apparatuses for collecting fluid from a patient during negative pressure wound therapy (NPWT). A first exemplary embodiment 100 of a fluid collection apparatus is shown in a front side view in FIG. 1A and cross-section view in FIG. 2A. An exploded view of apparatus 100 is shown in FIG. 4. Apparatus 100 comprises a first fluid pathway, such as chamber 122, defined by a fluid defining member, such as chamber tube 102, configured to be in fluid communication with a source of negative pressure through a first pathway within the chamber. Apparatus 100 further comprises a second fluid pathway defined by a second fluid defining member, such as a fluid inlet tube 115, configured to be in fluid communication with a wound site such that during NPWT, negative pressure exerted on the wound site allows fluid, such as air and exudate, from the wound to travel to the apparatus. Fluid drawn from the wound site travels via the second fluid pathway to a collection region 123 of the apparatus where fluid can be stored, while air drawn from the wound site can be preferentially drawn into the chamber 122 and toward the source of negative pressure. In some embodiments, the pathway defining member 115 is a fluid inlet tube. In some embodiments, the second fluid defining member is part of a cover 110 of the apparatus. In some embodiments, negative pressure is applied to draw fluid from the wound via the following pathway: the source of negative pressure draws air through a first opening 124, from a fluid pathway within tube 106 and filter assembly 101 within chamber 122, and from impeding element 103 from the second fluid path way defined by the fluid defining member 115 (and extension tube 107, if present), such that fluid comprising air and liquid is drawn to the apparatus from the wound via 125. From the perspective of the negative pressure from the wound site to the source of negative pressure, the pathway would be the reverse (e.g., negative pressure draws air from the wound site through second fluid defining pathway 125 defined by second fluid defining member 115, through impeding element 103, to first fluid pathway 122 defined by first fluid defining member 102, through filter assembly 101 within the first fluid pathway 122, through a third fluid pathway defined by a third fluid defining member 106 and out of the first opening 124 to the source of negative pressure. Fluid flow into the apparatus from the wound site is shown in FIG. 1A by the hatched arrows. Air flow into the source of negative pressure is shown in FIG. 1B by the white arrows.

Apparatus 100 houses chamber 122 and collection region 123 within an interior region formed by a cover 110 and collection vessel 111. Cover 110 comprises a first opening 124 configured to connect the apparatus to a source of negative pressure and to provide a first pathway in fluid communication between the chamber of the apparatus and the source of negative pressure. Cover 110 further comprises a second opening 125 configured to connect the apparatus to a wound dressing and to provide a second pathway in fluid communication between the wound site and the apparatus. As shown in FIG. 4, a sealing member 109 is optionally provided at the first opening 124 and second opening 125 to connect with the source of negative pressure and wound dressing, respectively. In some cases, the sealing member 109 comprises an O-ring. In some cases, the sealing member comprises a flat gasket, a Luer fitting, conical fit, or push fit mechanism or the like. However, other features may be provided to establish and maintain fluid communication between the apparatus and the wound dressing, as well as the apparatus and source of negative pressure. For example, collection vessel 111 may further comprise a non-detachable top with couplings or connections between the collection vessel and wound dressing, as well as the collection vessel and source of negative pressure.

Figure 2A:
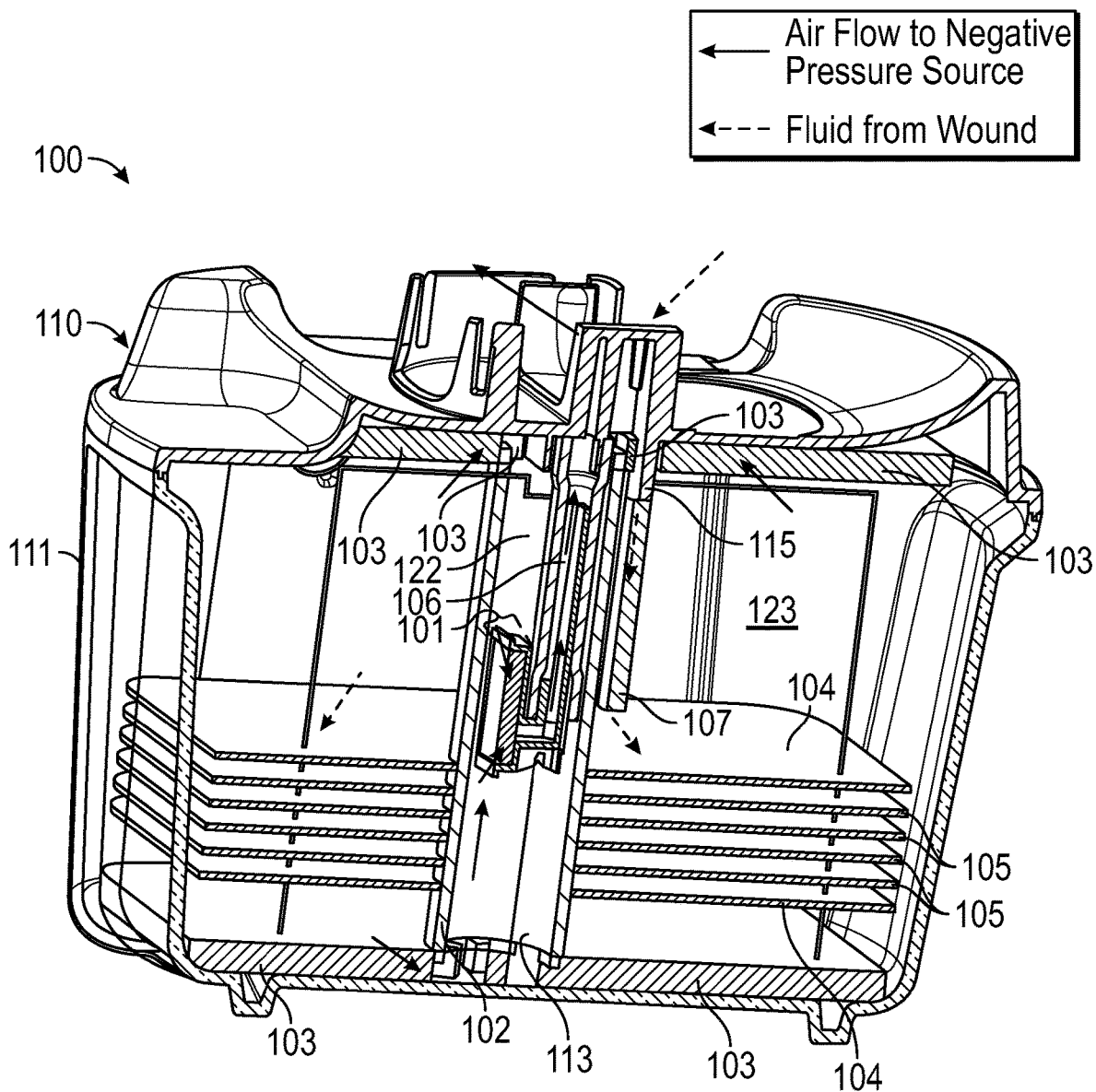
FIG. 2A depicts a cross-section view of the first embodiment of the fluid collection apparatus.

In an exemplary embodiment, air is preferentially drawn into the chamber 122 from the collection region 123 through a first impeding element 103 positioned at the top of the apparatus or a second impeding element 103 positioned at the bottom of the apparatus. Impeding elements 103 are shown in FIGS. 1-3. The first impeding element 103 is positioned at a first end of the chamber tube 102, and the second impeding element 103 is positioned at the second end of the chamber tube 102. In an exemplary embodiment, the first and second impeding elements are configured such that the pressure drop to draw liquid through the first and second impeding elements is higher than that to draw air through the first and second impeding elements. Accordingly, air may be preferentially drawn through the first or second impeding elements, through the chamber, and towards the source of negative pressure. The chamber tube 102 may be configured to hold the first and second impeding elements in place within the collection vessel 111. In some cases, the first impeding member may be pushed against cover 110 by the top of chamber tube 102 and the second impeding member may be pushed against the bottom of collection vessel 111 by the bottom of chamber tube 102, which compresses the first and second impeding members at the top and bottom sides of the chamber tube 102. In some cases, the impeding member may be compressed by about 100% to about 1000%. For instance, the impeding member is compressed from a thickness of about 3-10 mm to a thickness of about 0.5-5 mm. As a non-limiting example, the impeding member is compressed from a thickness of about 5 mm to a thickness of about 1 mm. For impeding members comprising a first uncompressed pore size, the compression of the first and/or second impeding members may reduce the uncompressed pore size by about 20% to about 80%. In some embodiments, the uncompressed pore size of the impeding element is from about 0.3 mm to about 0.5 mm. In some cases, the compressed pore size of the impeding element is from about 0.1 mm to about 0.2 mm. In some embodiments, the compressed pore size provides further preferential passage of air into the chamber as compared with liquid. The compressed pore size may also inhibit passage of particulates from wound fluid and/or absorbent material, if present, from entering into the chamber.

In some embodiments, the first and/or second impeding elements are configured to prevent the passage of particulates of about 100 microns to about 850 microns in size, e.g., about 400 microns in size. For a porous impeding element, the impeding element may comprise a tortuous path that hinders particulates smaller than the pore size from passing through the impeding element.

The impeding element may comprise an open-cell foam. In some cases, the foam comprises polyurethane, polyether, polyvinyl alcohol (PVA), or a combination thereof. For example, the impeding element comprises polyurethane foam. In some cases, the open-cell is compressed within the apparatus by the chamber tube 102, as described above. In some embodiments, the impeding element comprises a polypropylene, polyester, or rayon felt filter media such as supplied by Superior Felt and Filtration. In some cases, the impeding element comprises a polypropylene filter material, such as supplied by Pall Inc. In some embodiments, the impeding element comprises a fibrous material, for example, a polyester material. In some embodiments, the impeding element comprises a nonwoven material. Additional exemplary impeding elements are envisioned that comprise multiple small holes or capillaries through which air may preferentially pass during NPWT over liquid and/or particulate materials.

In some embodiments, the apparatus comprises an impeding element that is not positioned at either end of a chamber tube 102. As a non-limiting example, the impeding element is a series of small holes in a rigid structure e.g., radially holes or castellation slots through the wall of chamber tube 102 that may provide a fluid pathway that would provide resistance to liquid and preferential movement to air. In some such embodiments, chamber tube 102 may seal to the inside surface of the cover 110 and collection vessel 111. In some cases, the holes or slots are small enough to provide the appropriate flow resistance to liquid.

During NPWT, fluid is drawn into the collection region 123 through the pathway defining member 115 and optional fluid extension tube 107. Second fluid defining member 115 may extend to a desired length without the need for fluid extension tube 107, or may be connected to fluid extension tube 107 to establish an overall desired length of the two elements together. In a preferred embodiment, second fluid defining member 115 (with our without fluid extension tube 107) extends to a central region of collection region 123 to direct exudate and air to the central region. In some embodiments, the second fluid defining member 115 extends through the first impeding element. In other embodiments, the second fluid defining member 115 does not extend through the first impeding element. As a non-limiting example, the first impeding member may be formed such that wound fluid may pass into the collection region 123 without passing through the first impeding element. Collection region 123 may include an absorbent region comprising an absorbent material. Such absorbent material may be arranged as layers of absorbent material 105, and optionally wicking layers 104. If present, the wicking layers 104 are configured to transport liquid via capillary action through the wicking layers and into the layers of absorbent material to distribute fluid throughout the collection region 123. In some cases, the first and second impeding elements prevent the absorbent material from entering chamber 122.

Figure 5:
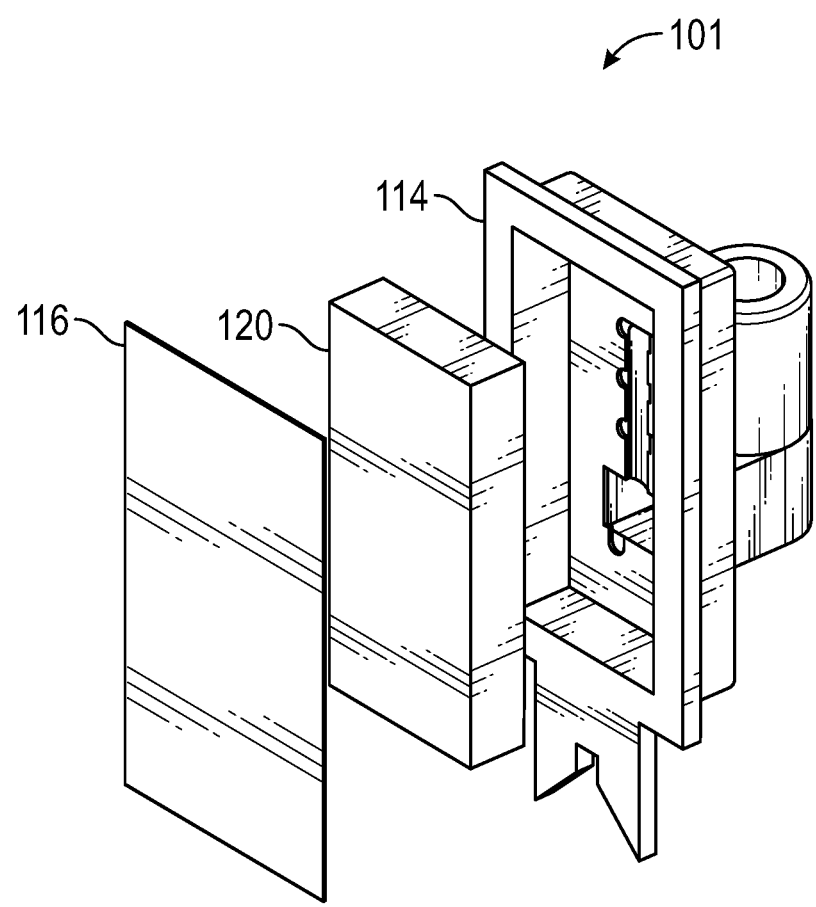
FIG. 5 depicts a filter assembly of various embodiments of a fluid collection apparatus.
Figure 6A:
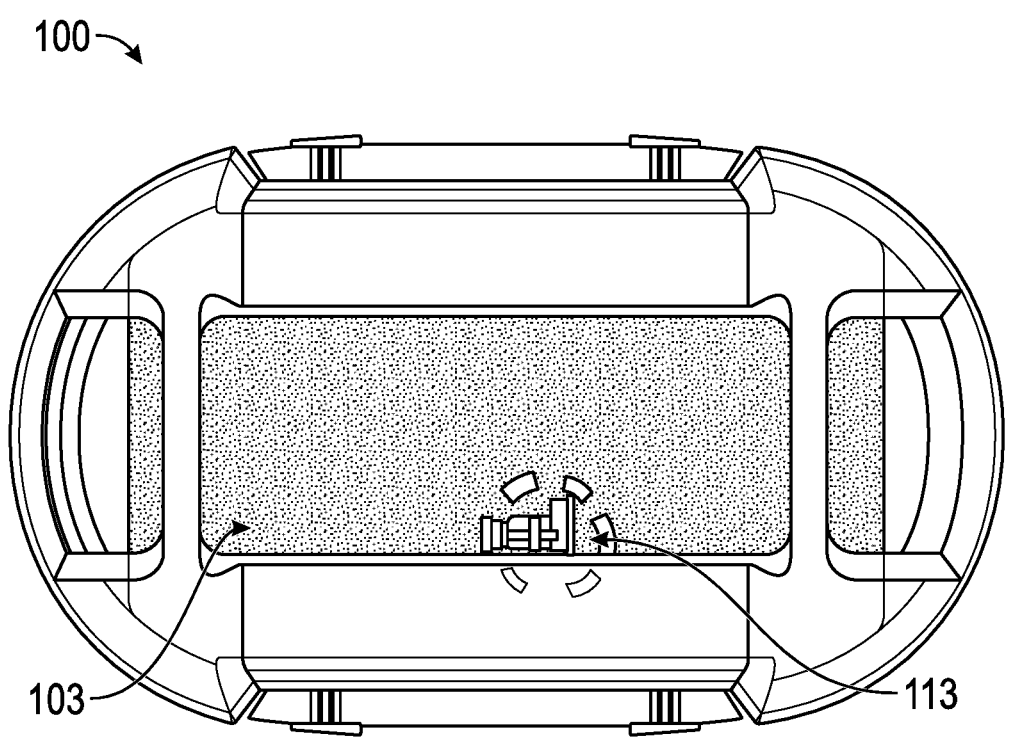
FIG. 6A depicts a bottom view of the first embodiment of the fluid collection apparatus.

Apparatus 100 further comprises a filter assembly 101, which is shown in an exemplary embodiment in FIG. 5. For example, filter assembly 101 comprises a filter housing 114, an air permeable filter 116, for example a hydrophobic filter or other suitable filter that traps or prevents liquid passage, and optionally an aromatic filter 120, e.g., an activated carbon filter or other suitable aromatic filter. The filter assembly 101 is positioned within chamber 122 by, for example, filter tube 106. In some embodiments, the filter tube 106 is sealed against the cover 110 to create the first air pathway between the chamber of the apparatus and the source of negative pressure. In some embodiments, the filter tube 106 is moulded to the cover 110. In some embodiments, the filter tube 106 is connected to a spigot, hole, or other portion of the cover 110 by, e.g., a push-fit or other suitable mechanism. In some cases, the filter assembly 101 and 106 may be connected to or part of cover 110. In some embodiments, where apparatus 100 does not include a cover 110, filter tube 106 may be connected (directly or indirectly) to a side of the apparatus such that air under negative pressure may be drawn through filter tube 106 to the source of negative pressure through an opening in the apparatus. As air is drawn into the chamber 122 through the first and second impeding elements during NPWT, air may flow through the air permeable filter 116 and the aromatic filter 120, into filter tube 106, and toward the source of negative pressure through opening 124. Filter assembly 101 may be supported within chamber 122 by a support 113. FIG. 6A shows a bottom view of an exemplary apparatus 100 showing support 113 within chamber 122, surrounded by the second impeding element 103.

During NPWT, a negative pressure source and wound dressing are connected to the apparatus such that fluid (including air and liquid exudate) is drawn from the wound into the apparatus by exerted negative pressure. Wound fluid enters the collection region 123 through opening 125, passing through second fluid defining member 115 and optional extension tube 107, following a path as generally depicted by the hashed arrows in FIG. 1A. The fluid may then be drawn into absorbent layers 105, e.g., by the optional wicking layers 104 where the fluid is retained. Air enters the apparatus with fluid from the wound through second fluid defining member 115 and optional extension tube 107. Air may be further drawn through the path generally shown by the white arrows in FIG. 1A. Air drawn into the first impeding element and/or second impeding element 103 into chamber 122, can travel through filters 116 and 120, through filter tube 106, and out of the apparatus toward the negative pressure source through opening 124, while the wicking and/or absorbent material are configured to retain exudate in the collection region 123. Air permeable filter 116 may hinder liquid from exiting the apparatus through filter tube 106 and proceeding to the source of negative pressure. To restrict undesired materials, such as absorbent/wicking material and non-liquid exudate, from reaching filter 116, filter assembly 101 may be protected from direct contact with such material. In this example, chamber tube 102 surrounds filter assembly 101 to restrict such undesired material from reaching the filter 116.

Figure 2B:
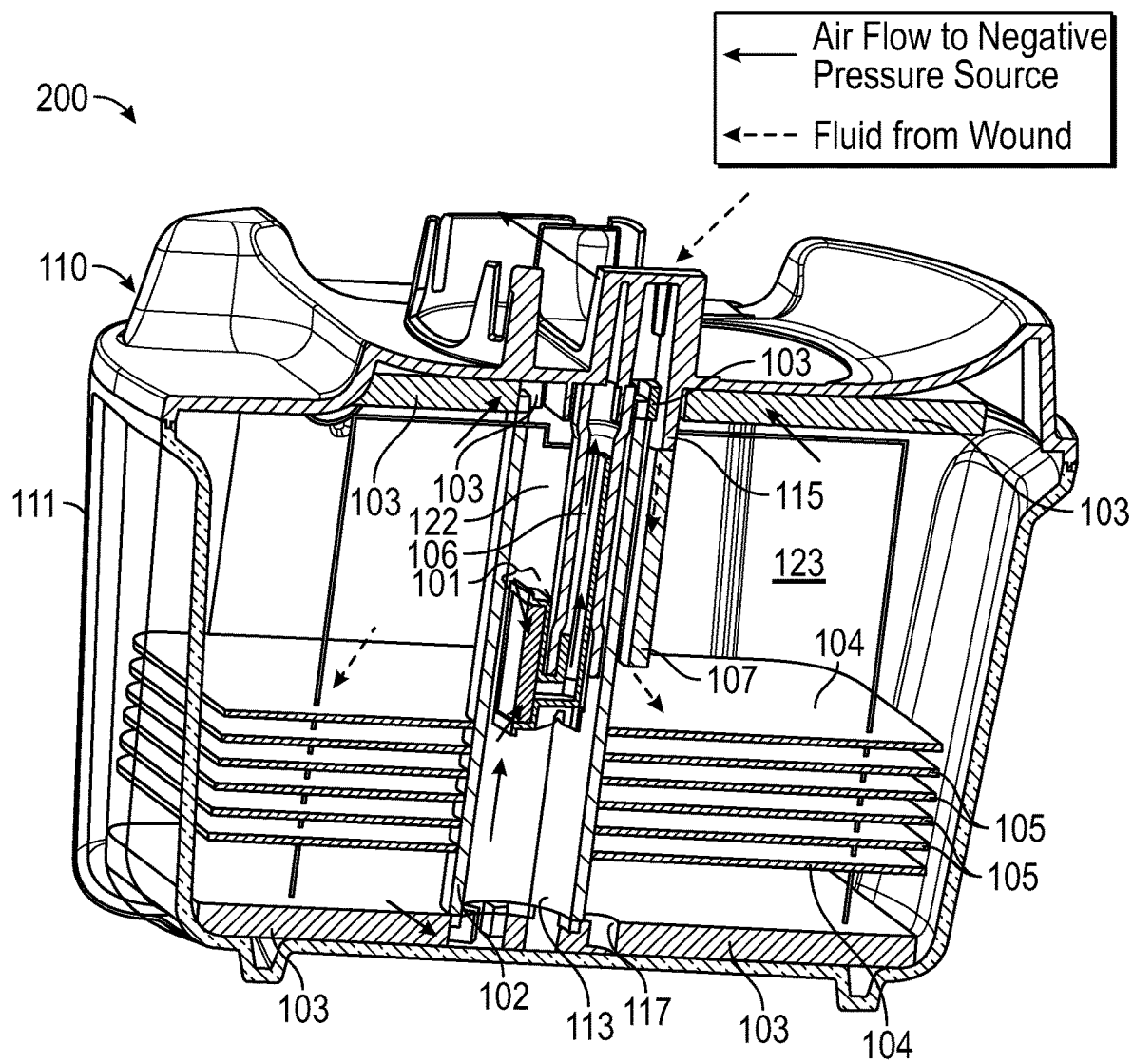
FIG. 2B depicts a cross-section view of the second embodiment of the fluid collection apparatus.
Figure 3A:
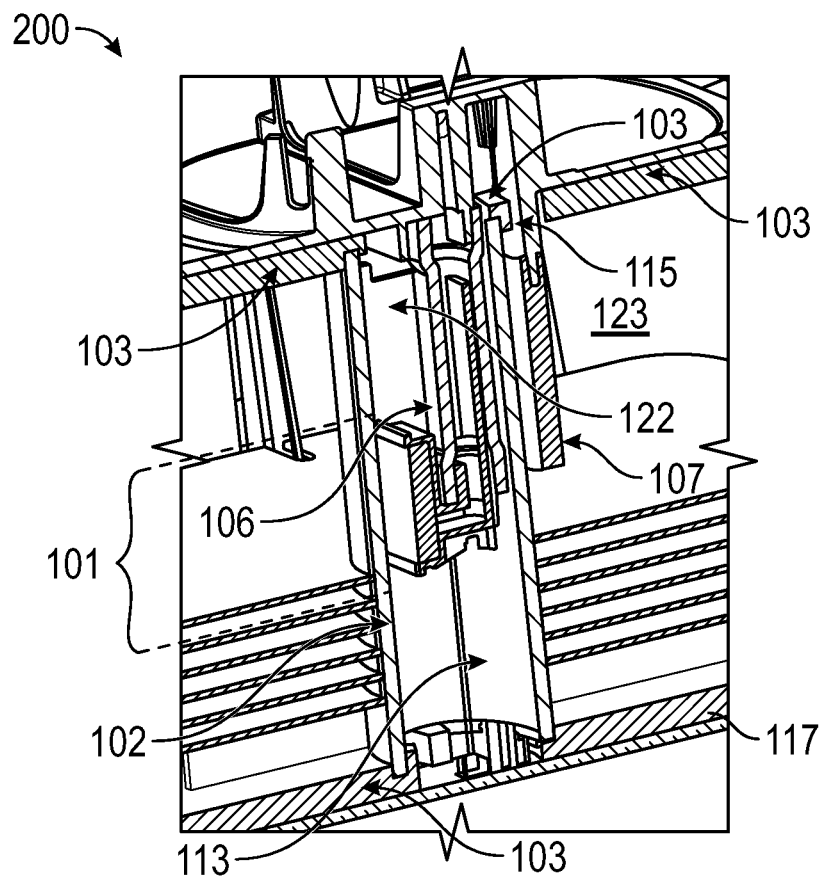
FIG. 3A depicts a detailed cross-section view of the first embodiment of the fluid collection apparatus.
Figure 3B:
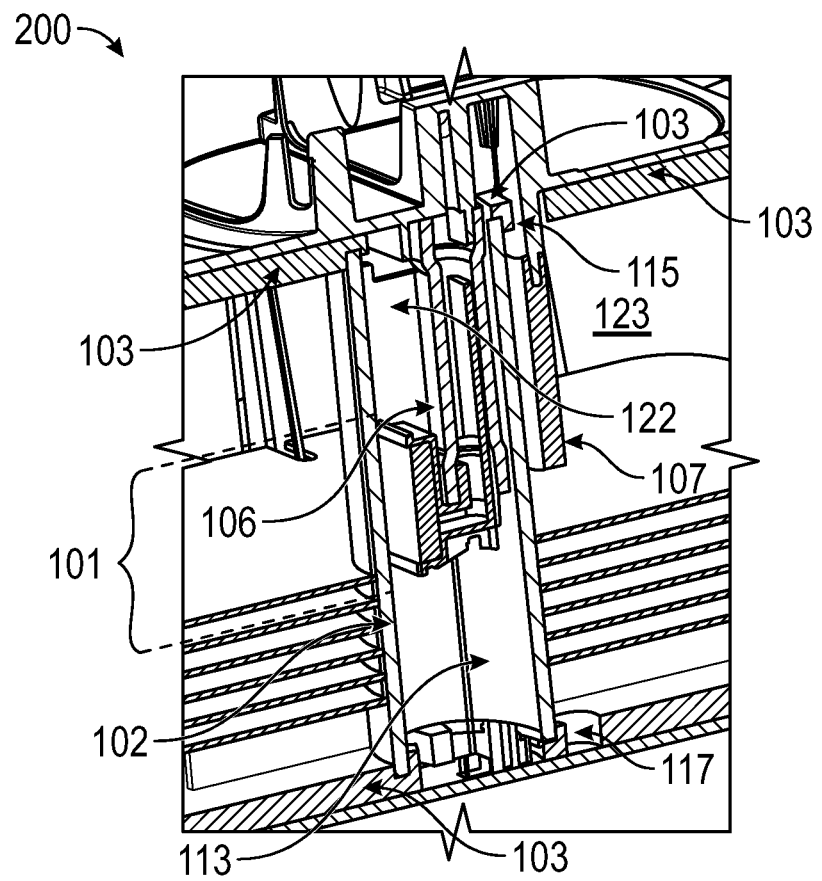
FIG. 3B depicts a detailed cross-section view of the second embodiment of the fluid collection apparatus.
Figure 6B:
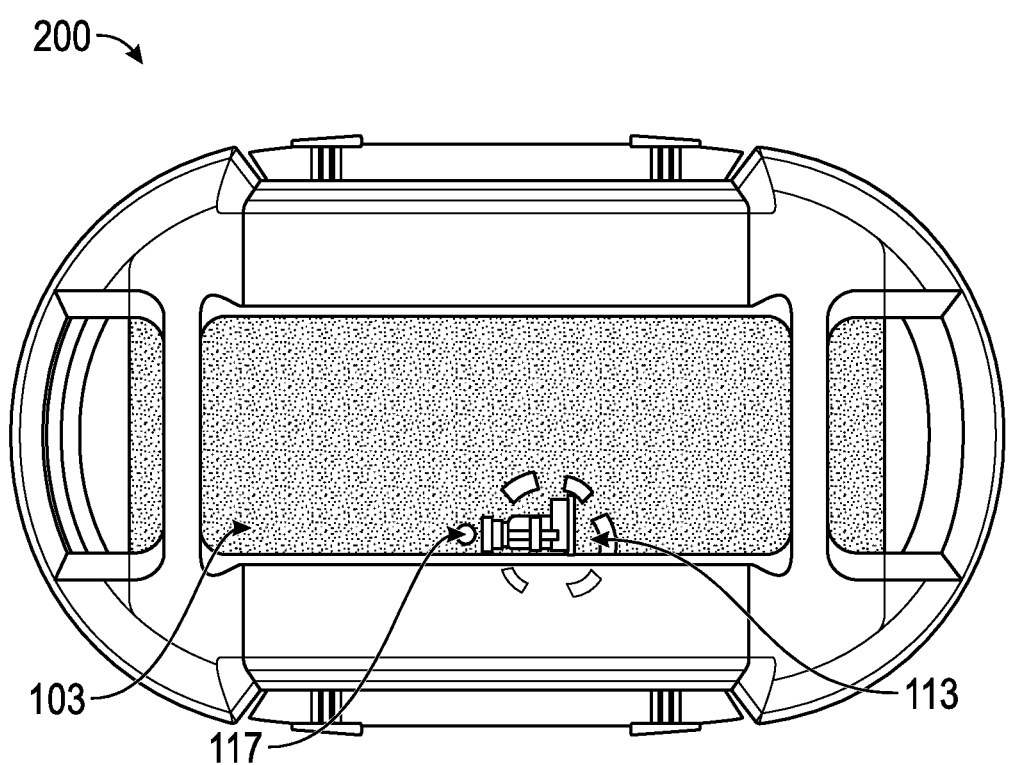
FIG. 6B depicts a bottom view of the second embodiment of the fluid collection apparatus.

A second embodiment 200 of a fluid collection apparatus is shown from a front side in FIG. 1B and as a cross-section in FIG. 2B. FIG. 3B shows a detailed cross-section view of the second embodiment as shown in FIG. 2B. Apparatus 200 comprises the general features of apparatus 100, except the impeding element 103 positioned at the bottom of the apparatus comprises a hole 117 similar to the hole in the impeding element 103 positioned at the top of the apparatus through which second fluid defining member 115 is passed. FIG. 6B shows the bottom side of the apparatus 200, showing the hole 117 in the impeding element 103, while FIG. 6A shows the bottom of the apparatus 100, where the impeding element does not comprise the hole 117. The figures show first and second impeding elements 103, the filter tube 106, and the optional fluid extension tube 107. As shown in the figures, filter tube 106 may be connected to cover 110 to create the first fluid pathway in fluid connection with the negative pressure source. The features of FIG. 2B correspond to the features of FIG. 2A, except the embodiment shown in FIG. 2A is lacking a hole 117 in the second impeding element 103.

Figure 7A:
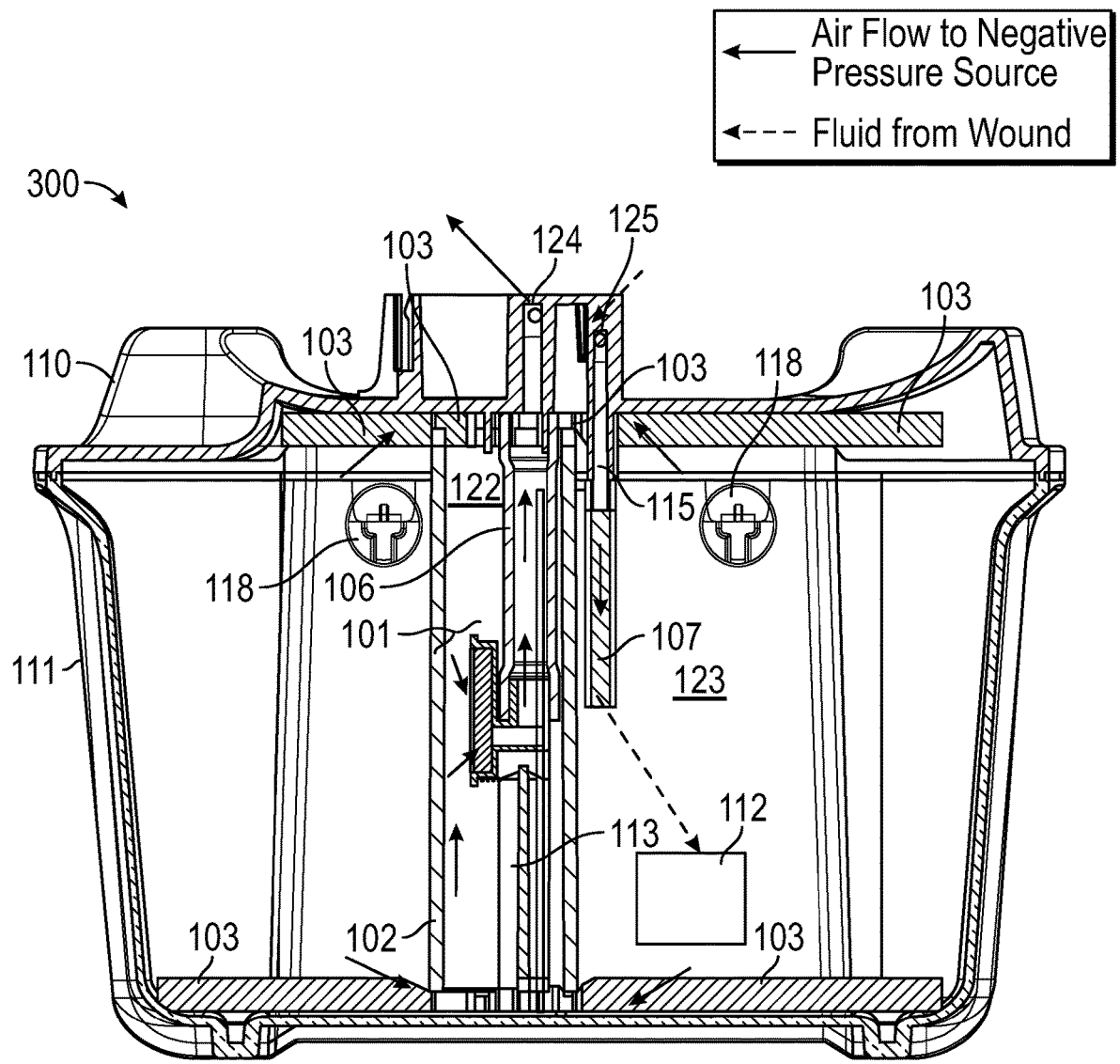
FIG. 7A depicts a front view of a third embodiment of a fluid collection apparatus.

A third embodiment of a fluid collection apparatus is shown in FIG. 7A as apparatus 300. Apparatus 300 comprises the general features of apparatus 100, except the absorbent region of apparatus 300 may, for example, comprise an absorbent material within a bag, pouch, or other container, for example, a sachet 112, as opposed to layers of absorbent material. In some cases, the superabsorbent container, for example, a sachet, is dissolvable. While the drawing depicts an exemplary embodiment of a single sachet, the apparatuses and devices as disclosed herein may comprise a plurality of containers comprising superabsorbent, including at least one superabsorbent container, at least two superabsorbent containers, at least three superabsorbent containers, at least four superabsorbent containers, at least five superabsorbent containers or more, depending in part, for example, on the volume and dimensions of the apparatus.

In still other embodiments, the collection region 123 comprises an absorbent material, for example, superabsorbent material, such as superabsorbent granules, particles or other material capable of absorbing large amounts of liquid exudate relative to its own mass. Examples of superabsorbent polymers include, but are not limited to, cellulose or cellulose-derivative, for example, carboxymethyl cellulose, polyacrylate, including sodium polyacrylate, polyacrylamide and polyacrylamide co-polymers, ethylene maleic anhydride copolymers, crosslinked-carboxymethylcellulose, polyvinyl alcohol copolymers, cross-linked polyethylene oxide, polyacrylonitrile copolymers and combinations thereof. Absorbent material, for example superabsorbent polymers, may optionally include materials capable of absorbing odors or other noxious elements present in exudate and/or other excipients needed to, for example, increase particle size or surface area. In some cases, an odour absorbing material, such as activated carbon particles, may be included or added into to an impeding element, and/or wicking layer to provide an additional means to control odour such that air passing through the apparatus passes over odour absorbing material such as activated carbon.

Figure 7B:
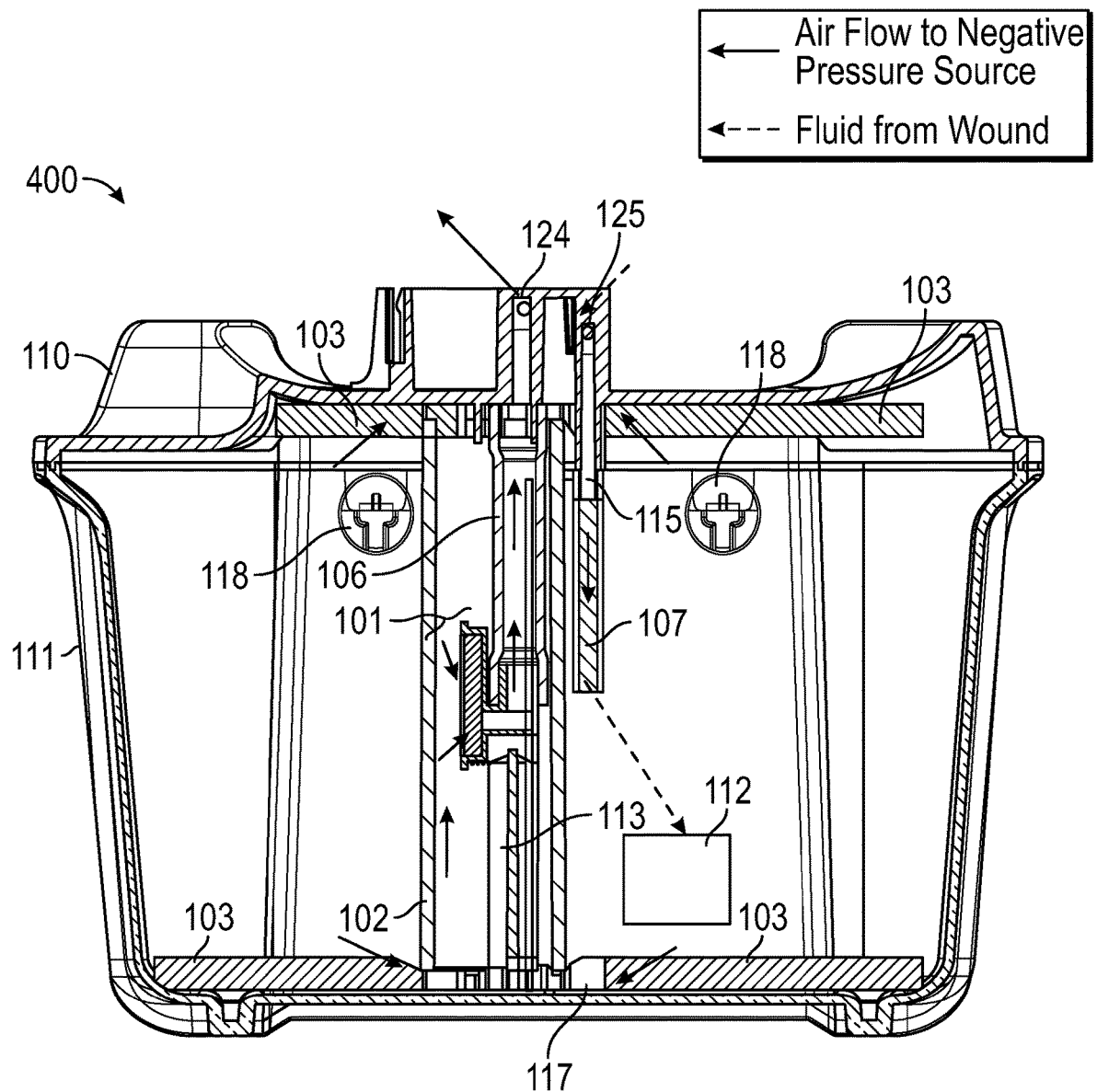
FIG. 7B depicts a front view of a fourth embodiment of a fluid collection apparatus.
Figure 8:
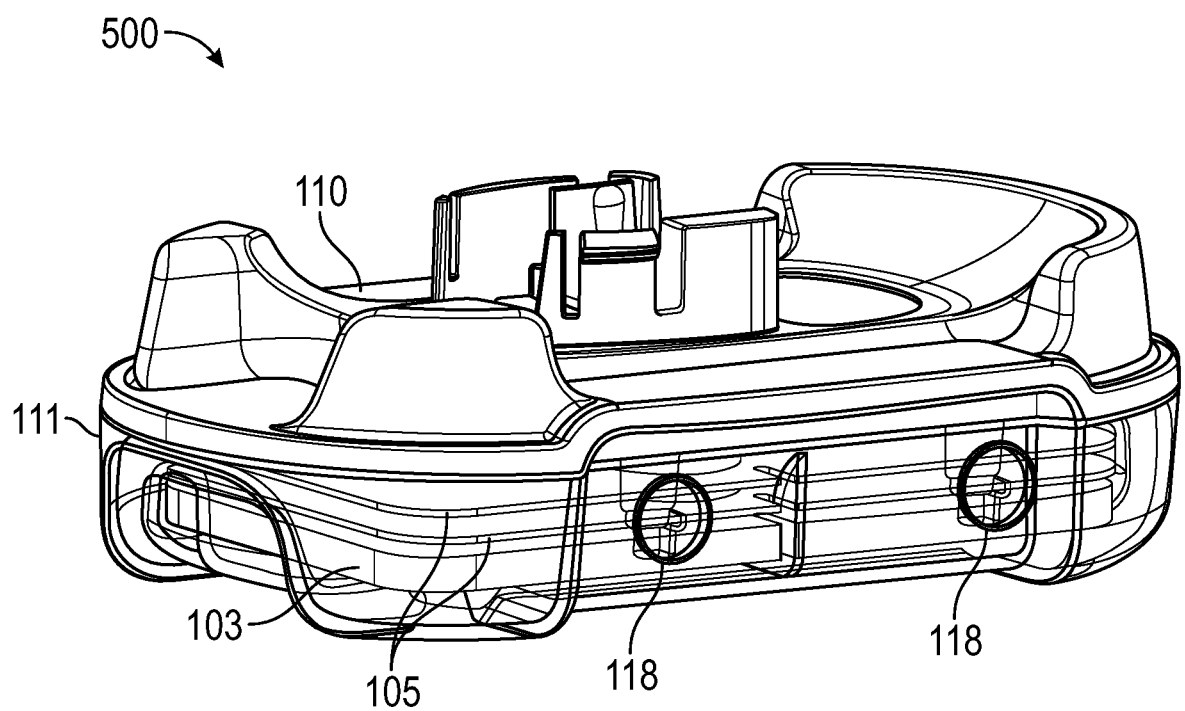
FIG. 8 depicts a perspective view of a fifth embodiment of a fluid collection apparatus.

A fourth embodiment of a fluid collection apparatus is shown in FIG. 7B as apparatus 400. Apparatus comprises the general features of apparatus 200, except the absorbent region of apparatus 400 comprises, for example, an absorbent material within a bag, pouch, or other container, for example, sachet 112.

Figure 9:
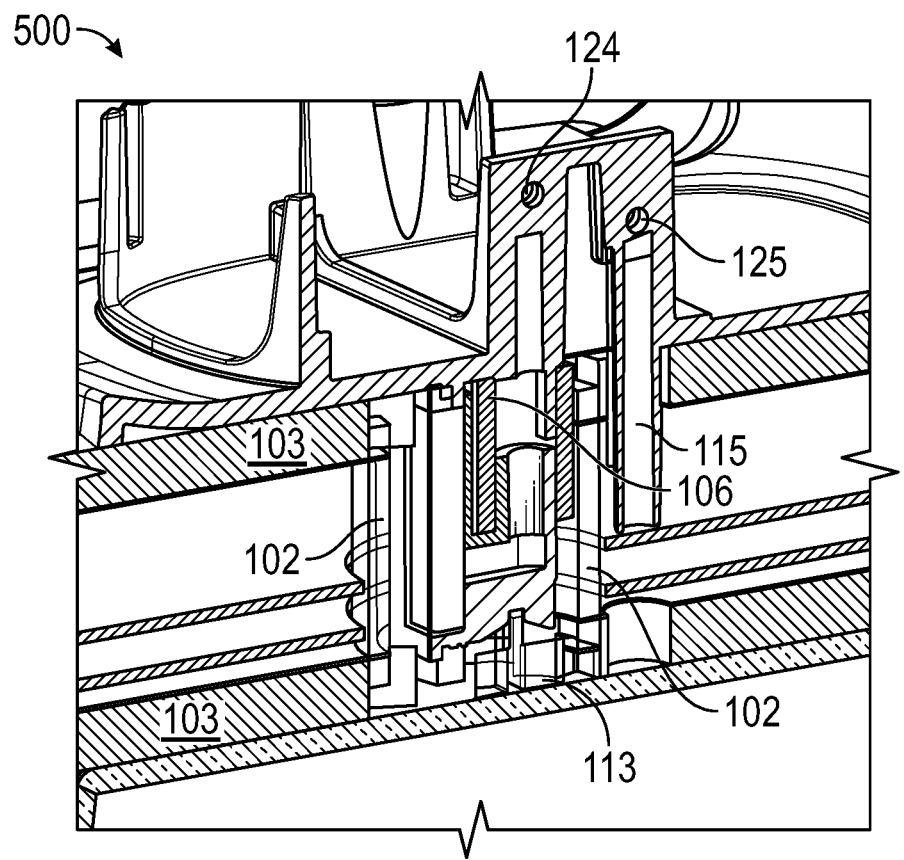
FIG. 9 depicts a detailed cross-section view of the fifth embodiment of the fluid collection apparatus.
Figure 10:
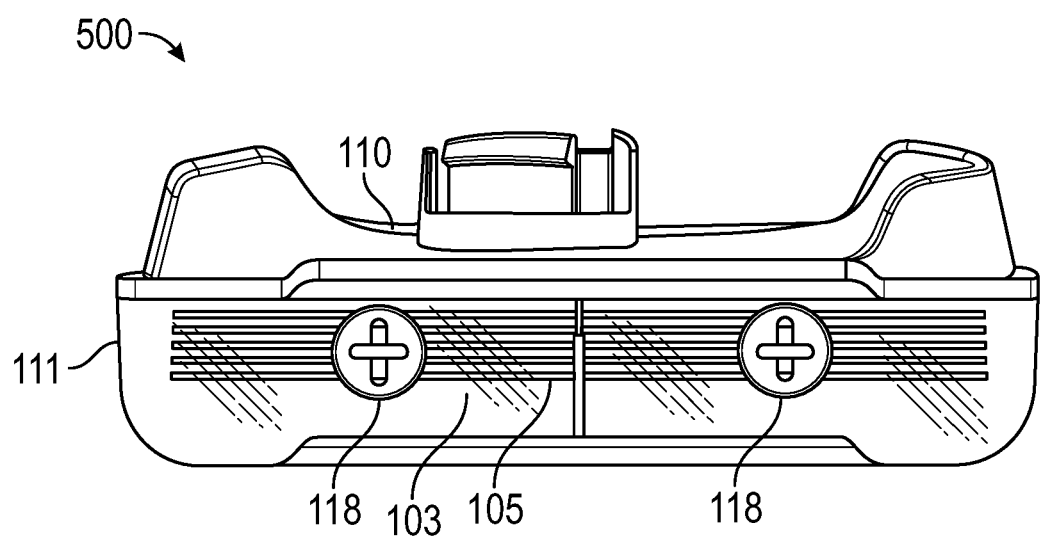
FIG. 10 is a photograph showing the front view of the fifth embodiment of the fluid collection apparatus.
Figure 11:
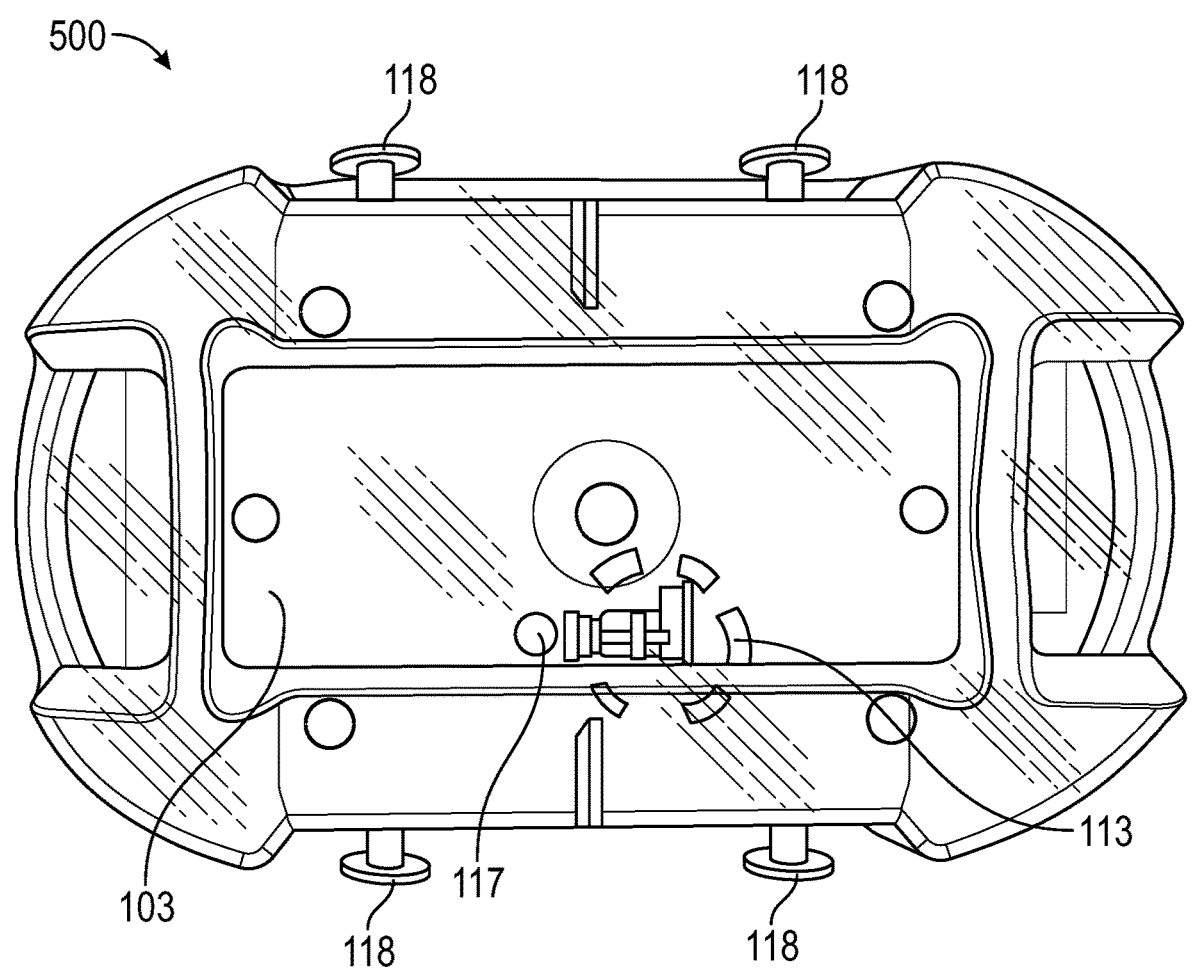
FIG. 11 is a photograph showing the bottom view of the fifth embodiment of the fluid collection apparatus.

A fifth embodiment of a fluid collection apparatus is shown in FIGS. 8-11 as apparatus 500. Apparatus 500 is configured to store a smaller volume than each of apparatuses 100, 200, 300 and 400. For example, apparatuses and devices disclosed herein may be configured to store from about 100 ml to about 500 ml, from about 100 ml to about 200 ml, or from about 100 ml to about 300 ml of liquid. As a non-limiting example, apparatus 500 is configured to store about 300 ml of liquid. In comparison, larger apparatuses 100, 200, 300, and/or 400 may be configured to hold from about 300 ml to about 1200 ml, from about 400 ml to about 1000 ml, from about 400 ml to about 900 ml, from about 500 ml to about 1200 ml, from about 500 ml to about 100 ml, from about 500 ml to about 900 ml, from about 600 ml to about 1200 ml, from about 600 ml to about 100 ml, or from about 600 ml to about 900 ml of liquid. As non-limiting examples, the larger apparatuses 100, 200, 300 and/or 400 may each hold about 600 ml or 900 ml of liquid. The smaller apparatus 500 further differs from larger apparatuses 100, 200, 300, and 400 by lacking an extension tube 107, as shown in FIG. 9. In FIG. 9, the impeding elements 103, the second fluid defining member 115 and cover 110, and the filter tube 106 are shown.

Figure 12A:
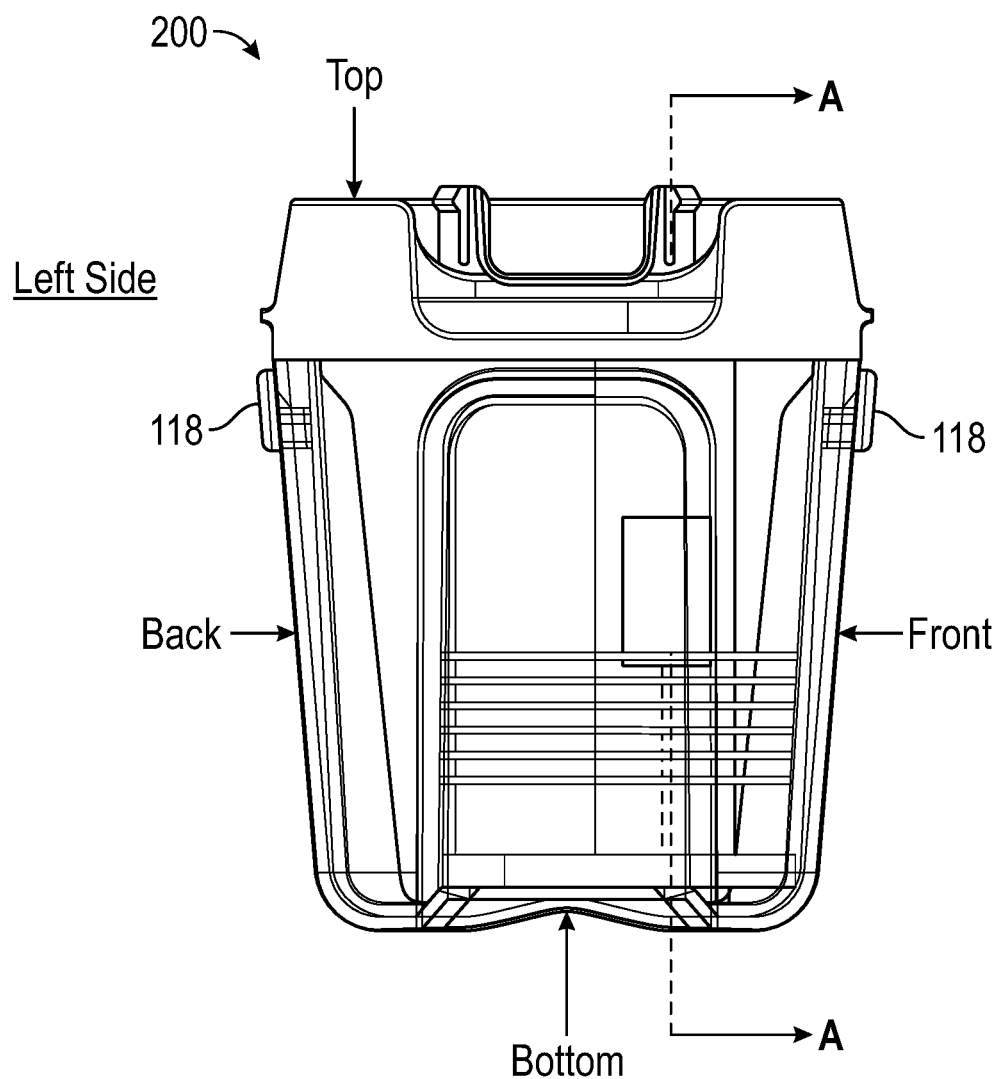
FIG. 12A shows the top, bottom, back, front, and left sides of the second embodiment of the fluid collection apparatus, as viewed from the left side of the apparatus.
Figure 12B:
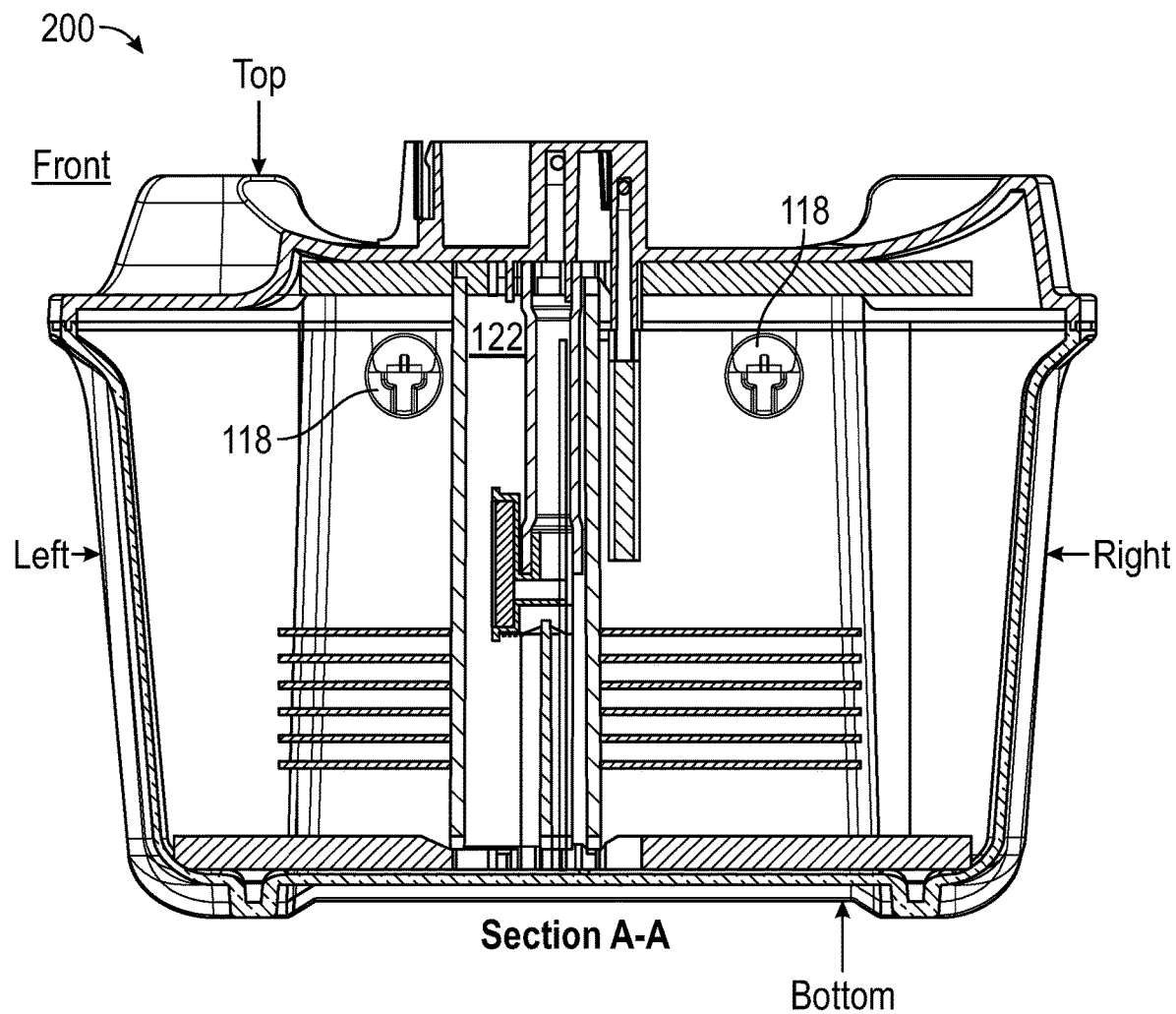
FIG. 12B shows the top, bottom, left, right, and front sides of the second embodiment of the fluid collection apparatus, as viewed from the front side of the apparatus.

Each of the apparatuses shown may comprise attachment points 118 for hanging each apparatus in storage and/or during NPWT from one or more of its sides. The sides of apparatus 100 are depicted in FIGS. 12A and 12B. Apparatus 100 comprises six sides: a top side, a bottom side, a front side, a back side, a left side, and a right side. In some cases, the apparatus may be hung from a drip stand or other vertical pole by, for example, any of the six sides. In some cases, the apparatus may be positioned on a horizontal or substantially horizontal surface on any of the six sides. In some cases, the apparatus may be positioned such that the top of the cover 110 is facing downward, e.g., either resting at least partially against a horizontal surface or hanging. For the first, second, and fifth embodiments, the absorbent layers 105 may shift when the apparatus is positioned on its cover 110. For example, the absorbent layers may move adjacent to the cover and collect liquid in this orientation. For the third and fourth embodiments, absorbent material 112 positioned within the bag, sachet, pouch or other housing may also shift when the orientation of the apparatus is changed. For example, absorbent material 112 may be positioned adjacent to any of the six sides that are facing downward during use.

The apparatus and features thereof shown in FIGS. 1-12 are for illustrative purposes only and it is intended that a fluid collection apparatus may comprise additional components and/or lack one or more components shown. For example, an absorbent material and/or wicking layer may not be necessary for the fluid collection apparatus to function as described. As another example, an extension tube may be optional.

As used herein, a fluid is inclusive of a liquid and/or gas. As a non-limiting example, fluid drawn into an apparatus during a negative pressure therapy may comprise a mixture of liquid and gas, and the liquid may be retained within a collection region of the apparatus. In some cases, a fluid comprising a mixture of liquid and gas may be retained within the collection region. In some cases, the collection region comprises an absorbent material configured to absorb and retain liquid from a fluid drawn into the collection region, where the fluid drawn into the collection region comprises the liquid or a mixture of the liquid and a gas. In further cases, at least some of a gas drawn into the collection region may be retained within that region. In other cases, while there may be no net increase of gas in the collection region during a negative pressure therapy, there may instead be a net decrease of gas in the collection region during negative pressure therapy.

Fluid Collection Apparatus

In one aspect, a fluid collection apparatus comprises a cover, a collection vessel, a chamber tube configured to be in fluid communication with a source of negative pressure, a first impeding element positioned at a first end of a first tube, a second impeding element positioned at a second end of the first tube, and a fluid inlet tube extending through the first impeding element. In some embodiments, the fluid inlet tube optionally comprises an extension such that the outlet end dispenses fluid drawn from a wound site of a patient during NPWT into a collection region of the collection vessel. In some instances, the first impeding element impedes fluid dispensed within the collection region from entering the first end of the first tube and the source of negative pressure. In some instances, the second impeding element impedes fluid dispensed within the collection region from entering the second end of the first tube and the source of negative pressure. The chamber tube may, for example, be configured to hold the first and the second impeding elements in place within the fluid collection apparatus. In some embodiments, the first and/or second impeding elements may comprise a material that allows air to flow freely within the material, while absorbing liquid exudate and/or restricting entry or movement of larger particles. In some embodiments, the impending element comprises foam, preferably an open cell foam. Exemplary foams include polyurethane, polyether, and polyvinyl alcohol (PVA). In some cases, the polyurethane foam is a reticulated polyurethane foam.

In one aspect, a fluid collection apparatus comprises a cover, a collection vessel, and an interior region comprising a chamber tube, a first impeding element positioned at a first end of the tube, a second impeding element positioned at a second end of the tube, and an absorbent material. In some instances, the absorbent material may be positioned external to the tube. In some embodiments, the first and second impeding elements may inhibit or prevent transfer of the absorbent material to the interior of the tube. In some embodiments, the first and/or second impeding elements may comprise foam; in other embodiments, the first and/or second impeding elements may comprise an open cell foam. Exemplary foams include polyurethane, polyether, and polyvinyl alcohol (PVA). In some cases, the polyurethane foam is a reticulated polyurethane foam.

In another aspect, a fluid collection apparatus comprises a cover, a collection vessel, a chamber tube, a first impeding element positioned at a first end of the tube, a second impeding element positioned at a second end of the tube, and a collection region external to the tube. In some embodiments, the first impeding element provides a first air path from the collection region to the interior of the tube, and the second impeding element provides a second air path from the collection region to the interior of the tube. In some embodiments, the first and/or second impeding elements may comprise foam; in other embodiments, the first and/or second impeding elements may comprise open cell foam. Exemplary foams include polyurethane, polyether, and polyvinyl alcohol (PVA). In some cases, the polyurethane foam is a reticulated polyurethane foam.

In another aspect, a fluid collection apparatus comprises a cover, a collection vessel, a fluid inlet tube, a fluid collection region, and at least one impeding element; wherein the fluid inlet tube optionally comprises an extension of an outlet end for dispensing fluid collected during negative pressure wound therapy into a fluid collection region of the collection vessel/In some embodiments, the fluid inlet tube extends through the impeding element such that the outlet end of the tube is positioned within the fluid collection region, and the outlet end of the tube is positioned adjacent to the absorbent region. In some instance, an optional extension may be provided to extend the outlet end of the fluid inlet tube such that the outlet end in larger apparatus configurations may be positioned adjacent to the absorbent region. In some embodiments, the first and/or second impeding elements may comprise foam; in other embodiments, the first and/or second impeding elements may comprise open cell foam. Exemplary foams include polyurethane, polyether, and polyvinyl alcohol (PVA). In some cases, the polyurethane foam is a reticulated polyurethane foam.

In one aspect, a fluid collection apparatus comprises a collection vessel, a fluid inlet tube, a fluid collection region, and at least one impeding element. In some instances, the fluid inlet tube optionally comprises an extension such that the outlet end of the fluid inlet tube is capable of dispensing fluid collected during negative pressure wound therapy into a fluid collection region of the collection vessel such that the outlet end of the fluid inlet tube may be positioned adjacent to or within the fluid collection region. In some instances, the outlet end of the fluid inlet tube may be positioned adjacent to an optional absorbent region. In yet other embodiments, the outlet end of the fluid inlet tube may be positioned within a region comprising, for example, superabsorbent material. In some instances, the superabsorbent may be contained within a bag, pouch or container, for example a sachet. In other instances, the bag, pouch or container may be dissolvable, for example, a dissolvable sachet. In some embodiments, the first and/or second impeding elements may comprise foam; in other embodiments, the first and/or second impeding elements may comprise open cell foam. Exemplary foams include polyurethane, polyether, and polyvinyl alcohol (PVA). In some cases, the polyurethane foam is a reticulated polyurethane foam.

In one aspect, a fluid collection apparatus comprises a collection vessel, a chamber tube configured to be in fluid communication with a source of negative pressure, a first impeding element positioned at a first end of a first tube, a second impeding element positioned at a second end of the first tube, and a fluid inlet tube extending through the first impeding element. In some embodiments, the fluid inlet tube optionally comprises an extension such that the outlet end dispenses fluid drawn from a wound site of a patient during NPWT into a collection region of the collection vessel. In some instances, the first impeding element impedes fluid dispensed within the collection region from entering the first end of the first tube and the source of negative pressure. In some instances, the second impeding element impedes fluid dispensed within the collection region from entering the second end of the first tube and the source of negative pressure. The chamber tube may, for example, be configured to hold the first and the second impeding elements in place within the fluid collection apparatus. In some embodiments, the first and/or second impeding elements may comprise a material that allows air to flow freely within the material, while absorbing liquid exudate and/or restricting entry or movement of larger particles. In some embodiments, the impending element comprises foam, preferably an open cell foam. Exemplary foams include polyurethane, polyether, and polyvinyl alcohol (PVA). In some cases, the polyurethane foam is a reticulated polyurethane foam. In some cases, the apparatus further comprises a cover configured to connect to the collection vessel.

In one aspect, a fluid collection apparatus comprises a collection vessel, and an interior region comprising a chamber tube, a first impeding element positioned at a first end of the tube, a second impeding element positioned at a second end of the tube, and an absorbent material. In some instances, the absorbent material may be positioned external to the tube. In some embodiments, the first and second impeding elements may inhibit or prevent transfer of the absorbent material to the interior of the tube. In some embodiments, the first and/or second impeding elements may comprise foam; in other embodiments, the first and/or second impeding elements may comprise an open cell foam. Exemplary foams include polyurethane, polyether, and polyvinyl alcohol (PVA). In some cases, the polyurethane foam is a reticulated polyurethane foam. In some cases, the apparatus further comprises a cover configured to connect to the collection vessel.

In another aspect, a fluid collection apparatus comprises a collection vessel, a chamber tube, a first impeding element positioned at a first end of the tube, a second impeding element positioned at a second end of the tube, and a collection region external to the tube. In some embodiments, the first impeding element provides a first air path from the collection region to the interior of the tube, and the second impeding element provides a second air path from the collection region to the interior of the tube. In some embodiments, the first and/or second impeding elements may comprise foam; in other embodiments, the first and/or second impeding elements may comprise open cell foam. Exemplary foams include polyurethane, polyether, and polyvinyl alcohol (PVA). In some cases, the polyurethane foam is a reticulated polyurethane foam. In some cases, the apparatus further comprises a cover configured to connect to the collection vessel.

In another aspect, a fluid collection apparatus comprises a collection vessel, a fluid inlet tube, a fluid collection region, and at least one impeding element; wherein the fluid inlet tube optionally comprises an extension of an outlet end for dispensing fluid collected during negative pressure wound therapy into a fluid collection region of the collection vessel/In some embodiments, the fluid inlet tube extends through the impeding element such that the outlet end of the tube is positioned within the fluid collection region, and the outlet end of the tube is positioned adjacent to the absorbent region. In some instance, an optional extension may be provided to extend the outlet end of the fluid inlet tube such that the outlet end in larger apparatus configurations may be positioned adjacent to the absorbent region. In some embodiments, the first and/or second impeding elements may comprise foam; in other embodiments, the first and/or second impeding elements may comprise open cell foam. Exemplary foams include polyurethane, polyether, and polyvinyl alcohol (PVA). In some cases, the foam is a reticulated polyurethane foam. In some cases, the apparatus further comprises a cover configured to connect to the collection vessel.

In another aspect, a fluid collection apparatus comprises a collection vessel; optionally, a cover connected to a first side of the collection vessel; a first fluid pathway in fluid communication with a source of negative pressure, the first fluid pathway positioned between: (i) a first impeding element positioned at an interior of the cover or interior of the first side of the collection vessel and a (ii) second impeding element positioned at an interior of a second side of the collection vessel opposing the first side, wherein the first impeding element and the cover or first side of the collection vessel are in substantially fluid tight communication; a filter positioned within the first fluid defining member and between the first impeding element and the second impeding element; and a second fluid pathway for introducing exudate into the collection vessel. In some embodiments, the first and second impeding elements serve as, for example, a pre-filter to inhibit liquid from reaching the filter positioned within the first fluid defining member. In some embodiments, the first and the second impeding elements are not hydrophobic filters. In some embodiments, the filter and the impeding elements do not comprise the same material. In some embodiments, the first and the second impeding elements preferentially allow passage of air to enter into the first fluid defining member, but as the collection vessel fills, some liquid may pass into the first fluid defining member. When sufficient liquid has entered into the first fluid defining member and covers the filter, a signal may be received indicating that the collection vessel could be full or at least about 50% full.

In some embodiments, any fluid collection apparatus described herein comprising an air permeable filter positioned within the chamber. In some cases, the air permeable filter comprises a hydrophobic filter. The air permeable filter may have a pore size of about 0.2 microns to 0.8 microns, or about 0.2 microns, 0.45 microns, or 0.8 microns. The air permeable filter may comprise polyethersulfone (PES), polytetrafluorethylene (PTFE) (e.g., as manufactured by Dow Corning), cellulose acetate, cellulose nitrate membranes, or a combination thereof. In some embodiments, the apparatus further comprises a carbon filter.

In some embodiments, any fluid collection apparatus described herein may comprise an absorbent material. The absorbent material may comprise a superabsorbent material. For example, the absorbent material may comprise a fibrous structure impregnated with the superabsorbent material. The superabsorbent material may, for example, also comprise cellulose or a cellulose-derivative. In some cases, the absorbent material comprises one or more layers of absorbent material. In some cases, the absorbent material may be provided within a sachet. The absorbent material may also be adjacent to a wicking layer.

In some embodiments any fluid collection apparatus described herein comprises six sides, and the fluid collection apparatus in use is configured to be: (a) positioned with any of the six sides against a horizontal surface, and/or (b) hung from an attachment point on any of the six sides.

Fluid Collection Apparatus Components

In some embodiments, a fluid collection apparatus comprises a collection vessel and a cover. In some embodiments, the collection vessel may not include a separate cover but instead form all sides or walls of the vessel itself. The collection vessel may comprise a rigid plastic, e.g., a gamma sterilisable polycarbonate. An exemplary polycarbonate is Makrolon 2458. The cover may also comprise a rigid plastic such as a gamma sterilisable polycarbonate. Exemplary polycarbonates are Makrolon 2458 and RAL 9016. The cover may also comprise an O-ring for connecting the apparatus to a source of negative pressure and/or wound dressing. The O-ring may comprise nitrile, silicone, ethylene propylene diene monomer (EPDM), Viton, or a combination thereof. In some cases, the O-ring is black EPDM 70 Shore A.

The collection vessel may be configured to hold from about 100 ml to about 1200 ml of liquid in a collection region, e.g., a region comprising an absorbing material. In some cases, the collection vessel may hold about 100 ml, about 200 ml, about 300 ml, about 400 ml, about 500 ml, about 600 ml, about 700 ml, about 800 ml, about 900 ml, about 1000 ml, about 1100 ml, and about 1200 ml. In some embodiments, apparatus 100 is configured to hold about 600 ml of liquid. In some embodiments, apparatus 100 is configured to hold about 900 ml of liquid. In some embodiments, apparatus 200 is configured to hold about 600 ml of liquid. In some embodiments, apparatus 200 is configured to hold about 900 ml of liquid. In some embodiments, apparatus 300 is configured to hold about 300 ml of liquid.

In some embodiments, the first and second impeding elements of the apparatus comprise foam. The foam may be in the form of a layer that provides an air path from the collection region of the canister to the chamber and on to the negative pressure source. The foam may also prevent transfer of absorbing material to the filter assembly. In some cases, the foam is an open cell foam. In some cases, foam comprises polyurethane, polyether, polyvinyl alcohol (PVA), or a combination thereof. In an exemplary embodiment, the foam comprises polyurethane, e.g., a reticulated polyurethane foam. An exemplary reticulated polyurethane foam is Blue RAL 5017.

In some embodiments, a fluid collection apparatus comprises an absorbent region comprising an absorbent material. In some cases, the absorbent material comprises one or more layers of absorbent material. In some cases, the absorbent material has about 1, 2, 3, 4, 5, 6, 7, 8, 9, or 10 layers of absorbent material. As an exemplary embodiment, the absorbent material has 6 layers of absorbent material. In some cases, the absorbent material is provided within a sachet. The sachet may be dissolvable.

In some aspects, an absorbent material comprises a super absorbent material. Non-limiting examples of super absorbent materials include a material or combination of materials that absorb about or at least about 10-, 20-, 30-, 40-, 50-, 60-, 70-, 80-, 90-, 100-, 120-, 140-, 160-, 180-, 200-, 250-, 300-, 400-, or 500-times the super absorbent material's weight in water. In some cases, a super absorbent material absorbs about 20-500 times its weight in water, or absorbs about 50-500 times its weight in water. When the super absorbent is used in a bag or sachet for retaining biological fluids having salinity such as exudates, the super absorbent fluid may absorb between about 4 and about 10 times its weight in a saline liquid.

In some aspects, an absorbent material expands from a first thickness to a second thickness upon absorption of fluid, wherein the second thickness is less than or equal to the maximum thickness of the absorbent material. In some embodiments, the first thickness refers to the thickness of the absorbent material prior to absorption of fluid during a negative pressure therapy. For example, the first thickness is the thickness of the expandable absorbent material supplied and/or stored with a fluid collection apparatus for use in negative pressure therapy. In some embodiments, the absorbent material is a super absorbent material that expands during absorption of fluid. In some cases, the first thickness of the expandable absorbent material is between about 3 mm and 15 mm, or between about 5 mm and 10 mm. In some cases, the maximum thickness is between about 15 mm and 50 mm, or between about 20 mm and 35 mm. In some cases, the maximum thickness of the expandable absorbent material is about 1.2-, 1.4-, 1.6-, 1.8-, 2-, 2.5-, 3-, 3.5-, 4-, 4.5- or 5-times the first thickness. In some cases, the maximum thickness of the expandable absorbent material is about 1.5-5, 1.5-4, 1.5-3, 1.5-2.5, or 1.5-2 times the first thickness.

Non-limiting examples of absorbent materials include polyacrylate, non-woven material, cellulose fibres, tissue paper, polyacrylamide copolymer, and combinations thereof. A non-woven material includes a polyester staple fibre. In a non-limiting example, an apparatus comprises the superabsorbent polymer polyacrylate. As another non-limiting example, an apparatus comprises the superabsorbent polymer Needlefelt type 0570N700400 (Technical Absorbents). In some cases, an apparatus comprises two or more materials with absorbing properties. In some cases, an apparatus comprises a mixture of super absorbent polymer and cellulose fibers. In some embodiments, an absorbent material comprises a base fibrous structure impregnated with super absorbing polymer particles. For example, Specificall cellulose Absorbent Pad 113.

In some embodiments, an absorbent material is in a powder or granular form within a bag or sachet. In some embodiments, the absorbent material is enclosed within a casing within the apparatus. In some embodiments, the absorbent material comprises a superabsorbent polymer. The casing is sometimes referred to as a transmissive material or layer which allows fluid to flow into the casing to the absorbent material, while retaining the absorbent material within the casing. In some cases, the transmissive material has a wicking property, where fluid transfer into the casing is facilitated by the wicking property of the transmissive material, for example, via capillary action. In other or additional cases, a separate and/or additional wicking layer is provided on an exterior of the casing to draw liquid into the casing to the absorbing material. In some cases, a layer of the transmissive material enclosing the absorbent material is between about 0.02 mm and 0.2 mm thick or between about 0.08 mm and 0.15 mm thick. Non-limiting examples of transmissive materials include non-woven polypropylene, cellulose fibres, non-woven HDPE and a combination thereof.

In some embodiments, an absorbent material is provided in the collection region of the apparatus as loose particles, e.g., superabsorbent particles that are not contained in a bag or casing and are not formed as layers.

In some aspects of the disclosure, a fluid collection apparatus comprises a wicking material. Wicking materials include materials configured to receive liquid and then rapidly transport the liquid, for example, via capillary action, to another material adjacent the wicking material. For instance, the wicking material receives liquid drawn into the collection region of the apparatus and then transfers the liquid to the absorbent material, where the absorbent material absorbs and retains the liquid. In some embodiments, a wicking material wicks more than 15 mm of water vertically over a time period of 24 hours. In some cases, the absorbent material is a superabsorbent polymer. In exemplary embodiments, the apparatus comprises a wicking material positioned adjacent an absorbent material described herein. Non-limiting examples of wicking materials include cellulose pulp, cotton, tissue paper, non-woven polyester, and a combination thereof. In some configurations, about a 0.05-10 mm, or about a 0.2-2 mm layer of wicking material is positioned adjacent to an absorbent material.

For an apparatus comprising an absorbent region comprising an absorbent material and optionally a wicking material, the distance between the fluid inlet tube or extension tube and the absorbent region may be from about 10 mm to about 60 mm. As a non-limiting example, for an apparatus configured to hold about 300 ml of liquid, the distance is about 15 mm. As another example, for an apparatus configured to hold about 600 ml of liquid, the distance is about 30 mm. As a further example, for an apparatus configured to hold about 900 ml of liquid, the distance is about 40 mm.

The first fluid defining member, or chamber tube, that provides space for the filter assembly may be rigid. This member may be cut from an extruded tube or moulded to suit a particular apparatus. As a non-limiting example, a first fluid defining member comprises clear polycarbonate, such as Makrolon 2458. In some embodiments, the first fluid defining member has a circular, square, rectangular, or other cross section. For an apparatus comprising a circular cross section, the filter assembly may be positioned within the chamber such that the face of the filter is held away from a wall to allow for free passage of air. In some cases, the inner diameter of the chamber tube is from about 10 mm to about 24 mm, from about 12 mm to about 24 mm, from about 14 mm to about 24 mm, from about 16 mm to about 24 mm, from about 18 mm to about 24 mm, from about 12 mm to about 22 mm, from about 12 mm to about 20 mm, or from about 12 mm to about 18 mm. As a non-limiting example, the inner diameter is about 18 mm. In some cases, the outer diameter of the chamber tube is from about 16 mm to about 28 mm, from about 18 mm to about 28 mm, from about 20 mm to about 28 mm, from about 22 mm to about 28 mm, from about 16 mm to about 26 mm, from about 16 mm to about 24 mm, or from about 16 mm to about 22 mm. As a non-limiting example, the outer diameter is about 22 mm. In some embodiments, the first fluid defining member may be permanently affixed or part of the cover or collection vessel.

The filter assembly may comprise an air permeable filter, an aromatic filter, and a filter housing. As a non-limiting example, the air permeable filter comprises a hydrophobic filter. In some cases, the filter housing is moulded in Natural ABS, e.g., as provided by Novodur FID M203FC. In some cases, the aromatic filter comprises carbon for reducing odors during NPWT. In some cases, the aromatic filter comprises from about 25 g/m2 to about 200 g/m2, from about 25 g/m2 to about 175 g/m2, from about 25 g/m2 to about 150 g/m2, from about 25 g/m2 to about 125 g/m2, from about 25 g/m2 to about 100 g/m2, from about 50 g/m2 to about 200 g/m2, or from about 75 g/m2 to about 200 g/m2 activated carbon. For example, the aromatic filter comprises about 80 g/m2, about 90 g/m2, or about 100 g/m2 activated carbon. An exemplary aromatic filter comprises activated carbon and a non-woven material with an enhanced binder. For instance, the non-woven blend comprises polyester, polyolefin, and activated carbon. As a non-limiting example, the non-woven blend comprises about 88% polyester and about 12% polyolefin, with about 90 g/m2 activated carbon (e.g., as provided by Sterling non-wovens, material number 3351).

In some embodiments, the air permeable filter has a pore size from about 0.2 microns and about 0.8 microns, or about 0.2 microns, about 0.45 microns, or about 0.8 microns. A first exemplary air permeable filter comprises polyethersulfone (PES). For example, a PES filter membrane on polyester nonwoven support, e.g., as provided by Pall, having material number S80535 (0.45 micron pore size, 0.76 mm to 0.162 mm thickness). The air permeable filter may alternatively or additional comprises polytetrafluorethylene (PTFE), cellulose acetate, cellulose nitrate membranes, or a combination thereof.

In some embodiments, the filter tube is elastomeric. In some embodiments, the filter tube is plastic. As non-limiting examples, the filter tube comprises gamma sterilisable materials such as polyvinyl chloride (PVC), silicone, ethylene propylene diene monomer (EPDM), Viton. In some cases, the filter tube comprises PVC 60 Shore A.

The apparatus may comprise a fluid inlet tube, and optionally, an extension tube. The extension tube, and/or fluid inlet tube, may comprise gamma sterilisable PVC, silicone, EPDM, Vitron, or a combination thereof. For example, the extension tube comprises PVC 60 Shore A. In some cases the extension tube attaches to the apparatus cover. In some cases, the extension tube is included in the cover moulding.

Systems and Kits

In one aspect of the disclosure, provided herein are systems comprising a fluid collection apparatus described herein and one or more accessory elements. Accessory elements include materials useful for performing a negative pressure therapy such as NPWT. In some embodiments, an accessory comprises a wound dressing. A wound dressing includes, without limitation, a dressing having a cover for sealing around a wound site and maintaining a negative pressure environment at the wound site, where the cover further comprises an adhesive for the sealing and an opening for the transfer of negative pressure. Non-limiting examples of wound dressing covers include polyurethane films having, for example, a polyurethane adhesive. In some embodiments, an accessory comprises a source of negative pressure. In some embodiments, "negative pressure" refers to pressure below atmospheric pressure. Sources of negative pressure include pumps configured to maintain a negative pressure between about 60 mmHg and about 145 mmHg below atmospheric pressure. For example, the pump may be configured to maintain a negative pressure of about 80, 100 or 125 mmHg below atmospheric pressure, ±20 mmHg. Sources of negative pressure include pumps configured to exert a maximum negative pressure of at least 200 mmHg, at least 330 mmHg or at least 400 mmHg. In exemplary embodiments, a pump is a diaphragm pump. In exemplary embodiments, a pump may be an electric pump, either mains or battery powered. The pump may be configured to operate continuously. In further exemplary embodiments, the pump may be a medical pump, such as a pump complying with Directive 93/42/EEC: IIA, IEC 60601-1 and/or IEC 60601-1-2. Additional accessory items include one or more conduits or tubings configured to connect the fluid collection apparatus to a source of negative pressure and/or wound dressing; and a connector configured to connect the outlet of the apparatus to a source of negative pressure, and connect the inlet of the apparatus to the wound dressing.

Methods

Provided herein are methods for collecting fluid using a fluid collection apparatus described herein. In some embodiments, the fluid collection apparatus utilized comprises a first fluid defining member, such as a chamber, in fluid communication with a source of negative pressure, a first impeding element positioned at a first end of the first fluid defining member, a second impeding element positioned at a second end of first fluid defining member, and a second fluid defining member, such as a fluid inlet tube, in fluid communication with a wound dressing; wherein the fluid inlet tube comprises an outlet end and the fluid inlet tube extends through the first impeding element such that the outlet of the fluid inlet tube is positioned within a fluid collection region of the fluid collection apparatus.

In one aspect, the method comprises applying a negative pressure from the source of negative pressure to the wound site via the fluid collection apparatus to draw fluid from the wound site, through the fluid inlet tube, and into the fluid collection region of the fluid collection apparatus; wherein the fluid comprises liquid and air, and the fluid is retained in the fluid collection region and the air is drawn through the first and/or the second impeding elements, into the interior of chamber tube, and towards the source of negative pressure. In some embodiments, the negative pressure applied from the negative pressure source is between about 75 mmHg and about 125 mmHg below atmospheric pressure.

In some methods, the fluid collection apparatus is positioned in an orientation-independent manner. In some cases, the fluid collection apparatus comprises multiple sides (e.g., six sides), and the fluid collection apparatus in use is: (a) positioned with any of the multiple sides against a horizontal surface and/or (b) hung or secured from an attachment point on any of the multiple sides. In some cases, the fluid collection apparatus is suspended, attached or otherwise secured from one or more attachment points on the fluid collection apparatus. In some cases, the orientation independence of an apparatus described herein is evaluated by filling the collection vessel with a liquid. In some cases, the liquid is water. In some cases, the liquid is a physiological saline solution. As a non-limiting example, the physiological saline solution is defined in EN13726-1 as Test solution A.

EXAMPLES

Example 1: Fluid Collection Apparatus

A fluid collection apparatus as generally depicted in FIG. 1 was manufactured. The components, canister header (110) and canister base (111) were injection moulded from suitable material. The chamber tube (102) was cut from extruded tube having a rigid material such as poly carbonate, or manufactured by injection moulding as a discrete component. The filter tube (106) and extension tube (107) were cut from a flexible tube material comprising PVC that had previously been extruded to shape. The filter assembly (101) was manufactured from three components: an outer housing (114), which was injection moulded from a plastic suitable for ultrasonic welding or thermally welding to the hydrophobic filter material (116), an activated carbon filter element (120) that is contained by the filter housing (114), and a hydrophobic filter (116) which is welded to the housing (114) to seal to the edges and retain the carbon filter.

The absorbent layers (105), foam (103) and wicking sheet (104) components were stamped from roll stock. The absorbent layers comprise superabsorbent polymers. A foam sheet (103), wicking sheet (104) and the absorbent layers (105) were loaded into the canister base (111) and the filter tube (106) was placed into the canister base so that it was located by alignment features in the base of the canister and trapped the foam sheet (103) and wicking sheet (104) against the base of the canister. The absorbent layers (105) were free to slide over the chamber tube (102). A foam sheet (103) and wicking sheet (104) were fitted to the canister header (110). The filter tube (106) was pressed onto the tube spigot of the filter housing of the filter sub assembly (101) and the opposite end of the filter tube (106) was pressed over the tube spigot of the header (110) so that the filter assembly (101) is connected to the header. Optionally the canister filling tube is fitted to the fluid inlet spigot on the canister header (110). The two partial assemblies (upper and lower) were brought together so that the filter assembly (101) fits within the canister tube (102) and the mating surfaces of the canister are brought together. In this example, the mating surfaces of the canister header (110) and canister base (111) have features to aid joining them together. In the case of ultrasonic welding being employed for the joining process, a weld concentrating feature is designed into one component and a receiving surface in the other. This feature pairing may be mating pair of a tongue and groove features on the mating surfaces with a small welding concentrator such as a small radius bump (0.2 to 1 mm diameter) on the end of the tongue feature to concentrate the welding energy. The assembly is typically placed in an ultrasonic welding feature and the two halves are welded together by application of ultrasonic energy to one component to form a seal with the other part. Optionally additional sealing can be provided by solvent or adhesive should this be necessary.

Example 2: Orientation Independence of a Fluid Collection Apparatus

To test the orientation independence of the apparatus, liquid representative of wound exudate was supplied to the apparatus at rate representative of anticipated use. This test was continued until the canister reached capacity and the hydrophobic filter was obscured by liquid. This test has been conducted with the apparatus in a typical orientation, with the canister resting on its base. This test has further been conducted with the canister placed on its side and on one end of the apparatus. The most challenging orientation is with the long axis at or close to vertical as this requires fluid to travel a greater vertical distance against gravity. However, the wicking layer assists performance under these conditions, ensuring that the majority of the absorbent layers were saturated before liquid reached the hydrophobic filter within the chamber tube.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the inventions described herein may be employed in practicing the inventions. It is intended that the following claims define a scope of the inventions and that methods and structures within the scope of these claims and their equivalents be covered thereby.

What is claimed is:

1. A fluid collection apparatus for negative pressure wound therapy comprising
   a collection vessel,
   a first fluid defining member having a chamber therein and configured to be in fluid communication with a source of negative pressure,
   a first impeding element formed of a porous material and positioned at a first end of the first fluid defining member,
   a second impeding element formed of a porous material and positioned at a second end of the first fluid defining member, and
   a second fluid defining member defining a pathway for dispensing fluid drawn from a wound site of a patient during negative pressure wound therapy into a collection region of the collection vessel; and
   wherein the first impeding element impedes fluid dispensed within the collection region from entering the chamber from a first end of the first fluid defining member and the source of negative pressure, and the second impeding element impedes fluid dispensed within the collection region from entering the chamber from a second end of the first fluid defining member and the source of negative pressure;
   wherein the first fluid defining member is positioned between the first impeding element and the second impeding element, wherein the first fluid defining member at least partially compresses the first impeding element and the second impeding element, thereby configured to hold the first impeding element and the second impeding element in place within the collection vessel.

2. The fluid collection apparatus of claim 1, wherein at least one of the first impeding element and the second impeding element comprises foam.

3. The fluid collection apparatus of any of claim 1, wherein at least one of the first and second impeding elements comprise polyurethane, polyether, polyvinyl alcohol (PVA), or a combination thereof.

4. The fluid collection apparatus of any of claim 1, further comprising a filter positioned within the chamber.

5. The fluid collection apparatus of claim 4, wherein the filter is a hydrophobic filter.

6. The fluid collection apparatus of claim 4, wherein the filter comprises a pore size of between about 0.2 micron to about 0.8 micron.

7. The fluid collection apparatus of claim 4, wherein the filter comprises polyethersulfone (PES), polytetrafluoroethylene (PTFE), cellulose acetate, or a cellulose nitrate membrane.

8. The fluid collection apparatus of claim 1, further comprising a carbon filter that comprises from about 25 g/m2 to about 200 g/m2 of activated carbon.

9. The fluid collection apparatus of claim 1, further comprising an extension element extending the second fluid defining member to an area adjacent to or within the collection region of the collection vessel.

10. The fluid collection apparatus of claim 1, wherein the first impeding element and the second impeding element are configured such that when the collection region of the collection vessel is filled with fluid to at least about 50% capacity by volume and sealed, in all orientations of the apparatus at least one of the first and second ends of the first fluid defining member is not submerged in liquid.

11. A multi-orientation fluid collection apparatus for negative pressure wound therapy comprising:
   a) a collection vessel comprising a first side and a second side,
   b) a cover connected to the first side of the collection vessel,
   c) a chamber tube defining a chamber having a first fluid pathway in fluid communication with a source of negative pressure, the chamber tube positioned between and in contact with:
      (i) a first impeding element formed of a porous material and positioned at an interior of the cover or interior of the first side of the collection vessel and a
      (ii) second impeding element formed of a porous material and positioned at an interior of the second side of the collection vessel, wherein the first impeding element and the cover or first side of the collection vessel are in substantially fluid tight communication, and wherein the second side is optionally opposing the first side;
   d) a filter positioned within the chamber of the chamber tube and between the first impeding element and the second impeding element, and
   e) a second fluid pathway for introducing exudate into the collection vessel
   wherein the chamber tube at least partially compresses the first impeding element and the second impeding element to at least partially hold the first impeding element and the second impeding element in place within the collection vessel.

12. The multi-orientation fluid collection apparatus of claim 11, wherein the filter hinders liquid from reaching the source of negative pressure.

13. The multi-orientation fluid collection apparatus of claim 11, wherein the filter is a hydrophobic filter that comprises a pore size of between about 0.2 micron to about 0.8 micron.

14. The multi-orientation fluid collection apparatus of claim 11, wherein the filter comprises polyethersulfone (PES), polytetrafluorethylene (PTEE), cellulose acetate, cellulose nitrate membranes, or a combination thereof.

15. The multi-orientation fluid collection apparatus of claim 11, wherein absorbent material is provided within a dissolvable sachet.

16. The multi-orientation fluid collection apparatus of claim 11, further comprising:
   a first wicking layer positioned between the first impeding element and an absorbent material; and
   a second wicking layer positioned between the absorbent material and the second impeding element.